United States Patent
Bharmi

(10) Patent No.: US 8,078,271 B2
(45) Date of Patent: Dec. 13, 2011

(54) SYSTEM AND METHOD FOR DISTINGUISHING BETWEEN HYPOGLYCEMIA AND HYPERGLYCEMIA USING AN IMPLANTABLE MEDICAL DEVICE

(75) Inventor: Rupinder Bharmi, Canyon Country, CA (US)

(73) Assignee: Pacesetter, Inc., Sylmar, CA (US)

( * ) Notice: Subject to any disclaimer, the term of this patent is extended or adjusted under 35 U.S.C. 154(b) by 471 days.

(21) Appl. No.: 12/406,791

(22) Filed: Mar. 18, 2009

(65) Prior Publication Data

US 2009/0177103 A1 Jul. 9, 2009

Related U.S. Application Data

(63) Continuation of application No. 11/127,370, filed on May 11, 2005, now Pat. No. 7,524,287, which is a continuation-in-part of application No. 11/043,612, filed on Jan. 25, 2005, now Pat. No. 7,502,644.

(51) Int. Cl.
*A61B 5/0402* (2006.01)
(52) U.S. Cl. .................................... 600/517; 600/365
(58) Field of Classification Search ............... 600/365, 600/517
See application file for complete search history.

*Primary Examiner* — Michael Kahelin

(57) ABSTRACT

Techniques are described for detecting and distinguishing among ischemia, hypoglycemia or hyperglycemia based on intracardiac electrogram (IEGM) signals. In one technique, these conditions are detected and distinguished based on an analysis of: the interval between the QRS complex and the peak of a T-wave (QTmax), the interval between the QRS complex and the end of a T-wave (QTend), alone or in combination with a change in ST segment elevation. By exploiting QTmax and QTend in combination with ST segment elevation, changes in ST segment elevation caused by hypo/hyperglycemia can be properly distinguished from changes caused by cardiac ischemia. In another technique, hyperglycemia and hypoglycemia are predicted, detected and/or distinguished from one another based on an analysis of the amplitudes of P-waves, QRS-complexes and T-waves within the IEGM. Appropriate warning signals are delivered and therapy is automatically adjusted.

10 Claims, 19 Drawing Sheets

SYSTEM AND METHOD FOR DISTINGUISHING BETWEEN HYPOGLYCEMIA AND HYPERGLYCEMIA USING AN IMPLANTABLE MEDICAL DEVICE

CROSS-REFERENCE TO RELATED APPLICATIONS

This application is a continuation of U.S. patent application Ser. No. 11/127,370 (now U.S. Pat. No. 7,524,287), filed May 11, 2005, entitled "System and Method for Distinguishing Between Hypoglycemia And Hyperglycemia Using an Implantable Medical Device," which is a continuation-in-part of U.S. patent application Ser. No. 11/043,612 (now U.S. Pat. No. 7,502,644), filed Jan. 25, 2005, entitled "System and Method for Distinguishing Among Cardiac Ischemia, Hypoglycemia And Hyperglycemia Using an Implantable Medical Device."

FIELD OF THE INVENTION

The invention generally relates to implantable medical devices such as pacemakers and implantable cardioverter/defibrillators (ICDs) and, in particular, to techniques for detecting cardiac ischemia, hypoglycemia and hyperglycemia using such devices and, more specifically, to techniques for more effectively detecting and distinguishing hypoglycemia from hyperglycemia.

BACKGROUND OF THE INVENTION

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less. Accordingly, it would be highly desirable to provide a technique for reliably detecting acute myocardial ischemia so that the victim may be warned and medical attention sought. If properly warned, surgical procedures may be implemented to locate and remove the growing arterial blockage or anti-thrombolytic medications may be administered. At the very least, advanced warning would allow the victim to cease activities that might result in a fatal accident. Moreover, in many cases, AMI or VF is triggered by strenuous physical activities and so advanced warning would allow the victim to cease such activities, possibly preventing AMI or VF from occurring.

Many patients at risk of cardiac ischemia have pacemakers, ICDs or other medical devices implanted therein. Accordingly, techniques have been developed for detecting cardiac ischemia using implanted medical devices. In particular, techniques have been developed for analyzing intracardiac electrogram (IEGM) signals in an effort to detect cardiac ischemia. See, as examples, the following U.S. patents: U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan, et al., 6,016,443, 6,233,486, 6,256,538, and 6,264,606 to Ekwall; 6,021,350 to Mathson; 6,112,116 and 6,272,379 to Fischell et al; 6,128,526, 6,115,628 and 6,381,493 to Stadler et al; and 6,108,577 to Benser. Most IEGM-based ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). The QRS complex usually follows an atrial depolarization (also referred to as a P-wave.) Strictly speaking, P-waves, R-waves and T-waves are features of a surface electrocardiogram (EKG). For convenience and generality, herein the terms R-wave, T-wave and P-wave are used to refer to the corresponding internal signal component as well.

A significant concern with any cardiac ischemia detection technique that relies on changes in the ST segments is that systemic influences within the patient can alter the ST segment. For example, hypoglycemia (low blood sugar levels) and hyperglycemia (high blood sugar levels) can both affect ST segment elevation. In addition, electrolyte imbalance, such as hypokalemia (low potassium levels) or hyperkalemia (high potassium levels) can affect the ST segment. Certain anti-arrhythmic drugs can also affect the ST-segment.

Accordingly, alternative techniques for detecting cardiac ischemia have been developed, which do not rely on ST segment elevation. One such technique is set forth in U.S. patent application Ser. No. 10/603,429, entitled "System And Method For Detecting Cardiac Ischemia Using An Implantable Medical Device", of Wang et al., filed Jun. 24, 2003, which is incorporated by reference herein. Rather than examine the ST segment, the technique of Wang et al. instead examines post-T-wave segments, i.e. that portion of the cardiac signal immediately following the T-wave. In one example, the onset of cardiac ischemia is identified by detecting a sharp falling edge within post-T-wave signals. A warning is then provided to the patient. The warning preferably includes both a perceptible electrical notification signal applied directly to subcutaneous tissue and a separate warning signal delivered via short-range telemetry to a handheld warning device external to the patient. After the patient feels the internal warning signal, he or she holds the handheld device near the chest to receive the short-range telemetry signal, which provides a textual warning. The handheld warning device thereby provides confirmation of the warning to the patient, who may be otherwise uncertain as to the reason for the internally generated warning signal. Another technique for detecting cardiac ischemia based on T-waves is set forth in U.S. patent application Ser. No. 10/603,398, entitled "System And Method For Detecting Cardiac Ischemia Based On T-Waves Using An Implantable Medical Device", of Min et al., filed Jun. 24, 2003, which is also incorporated by reference herein. With the technique of Min et al., cardiac ischemia is detected based either on the total energy of the T-wave or on the maximum slope of the T-wave. Again, if ischemia is detected, a warning signal is provided to the patient.

Hence, various cardiac ischemia detection techniques have been developed that exploit T-waves. Although these techniques are effective, it is desirable to provide still other T-wave-based ischemia detection techniques. It is also desirable to provide techniques that exploit deviations in the ST segment as well as changes in T-waves to provide further improvements cardiac ischemia detection. In particular, it is highly desirable to identify particular changes in T-waves that can be used to distinguish deviations in the ST segment caused by cardiac ischemia from changes caused by hypoglycemia or hyperglycemia or other systemic affects so as to improve the reliability and specificity of ST segment-based ischemia detection.

Although the detection of cardiac ischemia is of paramount importance since cardiac ischemia may be a precursor to a potentially fatal AMI or VF, it is also highly desirable to detect hypoglycemia or hyperglycemia, particularly within diabetic patients. Indeed, hypoglycemia is believed to be the cause of death in about three percent of insulin-treated diabetic patients. The putative mechanism for death due to hypoglycemia is a hypoglycemia-induced prolongation of the QT interval of the intracardiac electrogram (IEGM), which increases the risk of malignant ventricular tachycardia. See, for example, Eckert et al. "Hypoglycemia Leads to an Increased QT Interval in Normal Men", Clinical Physiology, 1998, Volume 18, Issue 6, Page 570 and also Heller, "Abnormalities of the Electrocardiogram during Hypoglycaemia: The Cause of the Dead in Bed Syndrome", Int. J. Clin. Pract. Suppl. 2002 July; (129): 27-32. Note that QT interval represents the portion of the IEGM between the beginning of ventricular depolarization and the peak of ventricular repolarization.

Hypoglycemia is also a serious and frequent problem in patients suffering hyperinsulinism, wherein the body generates too much insulin, thereby triggering episodes of hypoglycemia even if an otherwise sufficient amount of sugar or other glucose-generating substances are ingested. Medications appropriate for addressing hyperinsulinism included sulfonylureas, meglitinides, biguanides, thiazolidinediones, or alpha glucosidase inhibitors.

In adults, if not treated properly, severe hypoglycemia may result in coma and irreversible brain damage. McCarthy et al., "Mild hypoglycemia and impairment of brain stem and cortical evoked potentials in healthy subjects." Department of Pediatrics, Yale University School of Medicine, New Haven, Conn. 06510.

Even in cases where hypoglycemia does not cause severe consequences, it is often the limiting factor in achieving good glycemic control in patients with diabetes, particular insulin-depended diabetics. In this regard, patients sometimes refrain from taking prescribed dosages of insulin for fear that the insulin might trigger an episode of hypoglycemia, which can be unpleasant. Failure to take the prescribed insulin prevents the patient from maintaining glycemic levels within a healthy range, thus often leading to additional health problems.

Hyperglycemia, in contrast, is a condition characterized by abnormally high blood glucose levels. Often, hyperglycemia arises due to a lack of insulin within insulin-dependent diabetics. Hyperglycemia within diabetics can lead to ketoacidosis (i.e. diabetic coma), which can be fatal. Briefly, ketoacidosis occurs if the body lacks sufficient insulin to properly process the high blood glucose levels associated with hyperglycemia. Without sufficient insulin, the body cannot process glucose for fuel and hence breaks down fats to use for energy, yielding ketones as waste products. However, the body cannot tolerate large amounts of ketones and tries to eliminate the ketones through urine. Often, though, the body cannot eliminate the ketones and hence ketones build up in the blood leading to ketoacidosis. Excessively high ketone levels in the blood can be fatal.

Diabetic patients, hence, need to frequently monitor blood glucose levels to ensure that the levels remain within acceptable bounds and, for insulin dependent diabetics, to determine the amount of insulin that must be administered. Conventional techniques for monitoring blood glucose levels, however, leave much to be desired. One conventional technique, for example, requires that the patient draw blood, typically by pricking the finger. The drawn blood is then analyzed by a portable device to determine the blood glucose level. The technique can be painful and therefore can significantly discourage the patient from periodically checking blood glucose levels. Moreover, since an external device is required to analyze the blood, there is the risk that the patient will neglect to keep the device handy, preventing periodic blood glucose level monitoring. For insulin-dependent diabetics, failure to properly monitor blood glucose levels can result in improper dosages of insulin causing, in extreme cases, severe adverse health consequences such as a ketoacidotic diabetic coma, which can be fatal. Accordingly, there is a significant need to provide reliable hypo/hyperglycemia detection techniques, which do not rely on the patient to monitoring his or her own glucose levels and which does not require an external analysis device.

In view of the many disadvantages of conventional external blood glucose monitoring techniques, implantable blood glucose monitors have been developed, which included sensors for mounting directly within the blood stream. However, such monitors have not achieved much success as the glucose sensors tend to clog over very quickly. Thus, an implantable device that could continually and reliably measure blood glucose levels without requiring glucose sensors would be very desirable. Moreover, as with any implantable device, there are attended risks associated with implanting the blood glucose monitor, such as adverse reactions to anesthetics employed during the implantation procedure or the onset of subsequent infections. Hence, it is desirable to provide for automatic hypo/hyperglycemia detection using medical devices that would otherwise need to be implanted anyway, to thereby minimize the risks associated with the implantation of additional devices. In particular, for patients already requiring implantation of a cardiac stimulation device, such as a pacemaker or ICD, it is be desirable to exploit features of electrical cardiac signals.

It is now known that hypoglycemia can be detected based on observation of changes in the QT interval observed within an ECG (based on studies involving experimental hypoglycemia within adults with type 1 diabetes, i.e. insulin-dependent diabetes), as well as based on observation of dispersion of QT intervals within the ECG (based on studies involving experimental hypoglycemia within adults with type 2 diabetes, i.e. non-insulin dependent diabetes.) See, e.g., Landstedt-Hallin et al., "Increased QT dispersion during hypoglycaemia during hypoglycaemia in patients with type 2 DM." Studies in diabetics have also shown that hypoglycemia can be detected based on observation of a significant lengthening of the QTc interval occurring during spontaneous nocturnal hypoglycemia. See, Robinson et al., "Changes In Cardiac Repolarization During Clinical Episodes Of Nocturnal Hypoglycaemia In Adults With Type 1 Diabetes" Diabetologia. 2004 February; 47(2):312-5. Epub 2004 Jan. 8. The QTc interval is an adjusted version of the QT interval that has been corrected to a heart rate of 60 beats per minute (bpm). See, also, U.S. Pat. No. 6,572,542 to Houben, et al., entitled "System and Method for Monitoring and Controlling the Glycemic State of A Patient", which describes a technique exploiting a combination of ECG signals and electroencephalogram (EEG) for the detection of hypoglycemia.

See also U.S. Pat. No. 5,741,211 to Renirie, entitled "System And Method For Continuous Monitoring Of Diabetes-Related Blood Constituents." According to Renirie, in a non-diabetic subject, a glucose load, as results from food intake, leads to an increase in plasma glucose. In turn, the pancreas produces an increase in blood insulin. Following an increase in insulin, there is a cellular membrane change which results in infusion of potassium into the cells, and a subsequent decrease in blood potassium along with glucose uptake. The lowered extracellular potassium, or blood potassium, shortens the cardiac monophasic action potential, and produces a steeper monophasic action potential upstroke. This in turn results in observable ECG changes, such as the development of U-waves, ST segment depression, and in particular a shortening of the T-wave amplitude and a small increase in the R wave. Renirie is primarily directed to a Holter-type external monitor that analyzes the ECG but has some speculative discussions pertaining to implantable devices as well.

Although hyper/hypoglycemia detection techniques based on analysis of the ECG are somewhat helpful, there is a significant need to develop IEGM-based techniques for detecting and distinguishing between hyperglycemia and hyperglycemia, as well as improved IEGM-based techniques for detecting cardiac ischemia.

These and other problems were solved by the invention of the parent application cited above. Briefly, using the techniques of the parent application (which are also described herein-below) hypoglycemia is detected based on a change in ST segment elevation along with a lengthening of either the interval between the QRS complex and the end of a T-wave (QTmax) or the interval between the QRS complex and the end of the T-wave (QTend). Hyperglycemia is detected based on a change in ST segment elevation along with minimal change in QTmax and in QTend. Ischemia is detected based on a shortening QTmax, alone or in combination with a change in ST segment elevation. Alternatively, cardiac ischemia is detected based on a change in ST segment elevation combined with minimal change in QTend. By exploiting QTmax and QTend in combination with ST segment elevation, changes in ST segment elevation caused by hypo/hyperglycemia can be properly distinguished from one another and from changes caused by ischemia.

The following table summarizes changes in the ST segment, QTmax and QTend in response to hypoglycemia, hyperglycemia and cardiac ischemia that are exploited by the technique of the parent application.

TABLE I

|  | ST Segment | QTmax | QTend |
|---|---|---|---|
| Hypoglycemia | Significant deviation | Lengthens | Lengthens |
| Hyperglycemia | Significant deviation | Little or no change | Little or no change |
| Ischemia | Significant deviation | Shortens | Little or no change |
| Normal | No significant deviation | No significant deviation | No significant deviation |

Another useful technique is set forth in U.S. Patent Application Serial Number 2004/0077962 of Kroll, published Apr. 22, 2004, entitled "System and Method for Monitoring Blood Glucose Levels Using an Implantable Medical Device." The technique of Kroll is directed to detecting blood glucose levels based on IEGM signals sensed by an implantable medical device. Briefly, blood glucose levels are determined by an implantable device based on IEGM signals by detecting and examine a combination of T-wave amplitude fraction and QTc interval. The technique may also be used to detect hypoglycemia based on changes in blood glucose levels.

Yet another useful technique is set forth in U.S. patent application Ser. No. 11/117,624, of Bharmi filed Apr. 27, 2005, entitled "System and Method for Detecting Hypoglycemia Based on a Paced Depolarization Integral Using an Implantable Medical Device," which is assigned to the assignee of the present invention and is incorporated by reference herein. Briefly, techniques are provided therein specifically for detecting and tracking hypoglycemia. In one example, an implantable medical system tracks changes in a paced depolarization integral (PDI). A significant increase in PDI over a relatively short period of time indicates the onset of hypoglycemia. Upon detection of hypoglycemia, appropriate warning signals are generated to alert the patient. Certain therapies automatically provided by the implantable system may also be controlled in response to hypoglycemia. For example, if the patient is an insulin-dependent diabetic and the implantable system is equipped with an insulin pump capable of delivering insulin directly into the bloodstream, insulin delivery is automatically suspended until blood glucose levels return to acceptable levels. If the system includes an ICD, the ICD may be controlled to begin charging defibrillation capacitors upon detection of hypoglycemia so as to permit prompt delivery of a defibrillation shock, which may be needed if hypoglycemia triggers ventricular fibrillation.

Although the techniques described by Kroll and Bharmi as well as the techniques of the parent application are effective for detecting and distinguishing hypoglycemia and hyperglycemia, it would nevertheless be desirable to provide further improvements so as to provide improved detection specificity. By providing improved specificity in detecting hypoglycemia and hyperglycemia, any warning signals and any therapy delivered in response to hyper/hypoglycemia can be more reliably delivered. Furthermore, cardiac ischemia detection techniques of the type originally set forth in the parent application, which distinguish cardiac ischemia from hyper/hypoglycemia based on features of the IEGM, can also be more reliably performed. It is to this end that the invention of the present patent application is primarily directed. Moreover, still other aspects of the invention are directed to providing techniques for tracking changes in glycemic state so as to allow patients to achieve improved glycemic control. In particular, it is desirable to provide techniques for trending and tracking hyper/hypoglycemia in an effort to predict the onset of an episode of hypoglycemia in advance so as to warn the patient and still other aspects of the invention are directed to that end.

SUMMARY

In accordance with one illustrative embodiment, techniques are provided for use with an implantable medical device for distinguishing between hypoglycemia and hyperglycemia based on internal electrical cardiac signals (e.g. IEGMs). Briefly, an amplitude-based parameter representative of amplitudes of selected electrical events sensed within the heart of the patient is detected, and then hypoglycemia and hyperglycemia are distinguished from one another based on the amplitude-based parameter.

In one example, the selected electrical events include one or more of: atrial depolarization events (i.e. P-waves of the IEGM); ventricular depolarization events (i.e. QRS complexes of the IEGM); and ventricular repolarization events (i.e. T-waves of the IEGM). The amplitude-based parameter is representative of one or more of: the absolute values of the amplitudes of the selected electrical events; rates of change in the amplitudes of the selected electrical events over time; or beat by beat changes in the amplitudes of the selected electrical events.

Insofar as atrial depolarization events are concerned (i.e. P-waves of the IEGM), in the example, the implantable device associates the onset of hyperglycemia with a significant increase in the absolute value of the amplitudes of the atrial depolarization events, a significant rate of change in the amplitudes of the atrial depolarization events over time, and a significant beat to beat change in the amplitudes of the atrial depolarization events. Hypoglycemia is instead exhibits a lack of significant increase in the absolute value of the amplitudes of the atrial depolarization events, a lack of significant rate of change in the amplitudes of the atrial depolarization events over time, and a lack of significant beat to beat change in the amplitudes of the atrial depolarization events.

Insofar as ventricular repolarization events are concerned (i.e. T-waves of the IEGM), in the example, the implantable device associates the onset of hypoglycemia with a significant increase in the absolute value of the amplitudes of the ventricular repolarization events, a significant rate of change in the amplitudes of the ventricular repolarization events over time, and a significant beat to beat change in the amplitudes of the ventricular repolarization events. Hyperglycemia instead exhibits a lack of significant increase in the absolute value of the amplitudes of the ventricular repolarization events, a lack of significant rate of change in the amplitudes of the ventricular repolarization events over time, and a lack of significant beat to beat change in the amplitudes of the ventricular repolarization events.

Thus, the changes manifest in P-waves due to hyperglycemia and hypoglycemia are essentially reversed in T-waves. In other words, whereas the onset of hyperglycemia triggers a significant and rapid increase in P-wave amplitude, it is hypoglycemia that instead triggers a significant and rapid increase in T-wave amplitude. Conversely, whereas hypoglycemia yields no significant increase in P-wave amplitude, it is hyperglycemia that yields no significant increase in T-wave amplitude. Hence, a comparative analysis of P-wave and T-wave amplitudes observed within the IEGM is particularly useful for distinguishing hyperglycemia from hypoglycemia.

Insofar as ventricular depolarization events are concerned (i.e. QRS complexes of the IEGM), in the example, the implantable device associates the onset of hyperglycemia with: a greater increase in the absolute value of the amplitudes of the ventricular depolarization events than occurring with hypoglycemia; a greater rate of change in the amplitudes of the ventricular depolarization events over time than occurring with hypoglycemia; and a greater beat to beat change in the amplitudes of the ventricular depolarization events than occurring with hypoglycemia. Thus, although both hyperglycemia and hypoglycemia manifest an increase in the amplitude of the QRS complex, the increase is both greater and more rapid during the onset of hyperglycemia than during the onset of hypoglycemia. Hence, an analysis of the amplitude of QRS-complex is also helpful for distinguishing hyperglycemia from hypoglycemia.

The following table summarizes changes in the atrial depolarization, ventricular depolarization and ventricular repolarization amplitudes in response to hypoglycemia and hyperglycemia that are exploited by the invention.

TABLE II

|  | HYPERGLYCEMIA | HYPOGLYCEMIA |
|---|---|---|
| Atrial Depolarization: Amplitude | Significant increase | No significant change |
| Atrial Depolarization: Rate of Change of Amplitude (with Time or Beat by Beat) | Rapid increase | No significant change |
| Ventricular Depolarization: Amplitude | Significant increase | Moderate significant increase |
| Ventricular Depolarization: Rate of Change of Amplitude (with Time or Beat by Beat) | Rapid increase | Less rapid increase |
| Ventricular Repolarization: Amplitude | No significant change | Significant increase |
| Ventricular Repolarization: Rate of Change of Amplitude (with Time or Beat by Beat) | No significant change | Rapid increase |

Analysis of changes in the ST segment, QTmax and/or QTend can additionally be used to help distinguish hypoglycemia from hyperglycemia.

In accordance with another aspect of the invention, techniques are provided for directly detecting hyperglycemia based on selected amplitude-based parameters or for directly detecting hypoglycemia based on selected amplitude-based parameters. In one example, hyperglycemia is detected by: detecting a depolarization amplitude-based parameter representative of amplitudes of selected electrical depolarization events sensed within the heart of the patient; detecting a repolarization amplitude-based parameter representative of amplitudes of electrical repolarization events sensed within the heart of the patient; and then detecting hyperglycemia based on a significant increase in the depolarization amplitude-based parameter combined with a lack of significant change in the repolarization amplitude-based parameter. The depolarization amplitude-based parameter may be based on one or more of: atrial depolarization events and ventricular depolarization events. Hypoglycemia is detected by: detecting an atrial depolarization amplitude-based parameter representative of amplitudes of electrical atrial depolarization events sensed within the heart of the patient; detecting a repolarization amplitude-based parameter representative of amplitudes of electrical ventricular repolarization events sensed within the heart of the patient; and then detecting hypoglycemia based on a significant increase in the repolarization amplitude-based parameter in combination with lack of significant change in the atrial depolarization amplitude-based parameter.

Upon detecting and distinguishing hypoglycemia and/or hyperglycemia, appropriate warning signals are generated, which may include perceptible signals applied to subcutaneous tissue or short range telemetry warning signals transmitted to a device external to the patient, such as a bedside monitor. In one example, once a subcutaneous warning signal is perceived, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal. Upon confirmation of the warning, the patient then takes appropriate actions, such as ingesting foods suitable for increasing blood glucose levels in response to hypoglycemia or taking additional insulin in response to hyperglycemia.

Certain therapies automatically provided by the implantable device may also be initiated or modified in response to hypoglycemia or hyperglycemia. If the patient is an insulin-dependent diabetic and the implantable device is equipped with a drug pump capable of delivering insulin directly into the bloodstream, insulin delivery by the pump is automatically suspended during hypoglycemia until blood glucose levels return to acceptable levels. Insulin delivery is automatically increased during hyperglycemia, again until blood glucose levels return to acceptable levels. If the patient suffers hyperinsulanism and if the drug pump is equipped to deliver medications appropriate to hyperinsulinism, delivery of such medications is titrated in response to the glycemic state. In addition, if the device is an ICD, it may be controlled to begin charging defibrillation capacitors upon detection of hypoglycemia so as to permit prompt delivery of a defibrillation shock, which may be needed if hypoglycemia triggers VF due to a prolongation of the QT intervals. Additionally, or in the alternative, data representative of episodes of hyper/hypoglycemia or trend information pertaining to the amplitude-based parameters used to detect the episodes are stored for subsequent physician review, such as date/time and duration of the episode, the individual amplitude values detected, and any therapies automatically delivered. Trend information allows the patient and physician to develop and implement strategies for achieving better glycemic control within the patient.

Also, preferably, the recorded information is used to predict episodes of hyper/hypoglycemia so that warning signals may be generated to alert the patient to take appropriate action to prevent the episode from occurring. In one example, the prediction is performed by identifying a trend in increasing atrial depolarization amplitude. For example, if the recorded data indicates that the patient frequently has episodes of hyperglycemia early in the morning and atrial depolarization amplitude levels are found to be significantly increasing early on a particular morning, then a warning signal is issued notifying the patient that an episode of hyperglycemia is likely.

Hence, improved techniques are provided for reliably predicting, detecting and distinguishing hypoglycemia and hyperglycemia. The techniques are preferably performed by the implanted medical device itself so as to provide prompt warnings, if needed. Alternatively, the techniques may be performed by external devices, such as bedside monitors or the like, based on IEGM signals detected by an implanted device then transmitted to the external device. Other detection techniques, such as PDI-based techniques or QT interval-based techniques may be exploited in combination with the techniques of the invention to enhance detection specificity.

BRIEF DESCRIPTION OF THE DRAWINGS

Further features and advantages of the invention may be more readily understood by reference to the following description taken in conjunction with the accompanying drawings, in which.

Figure 2:
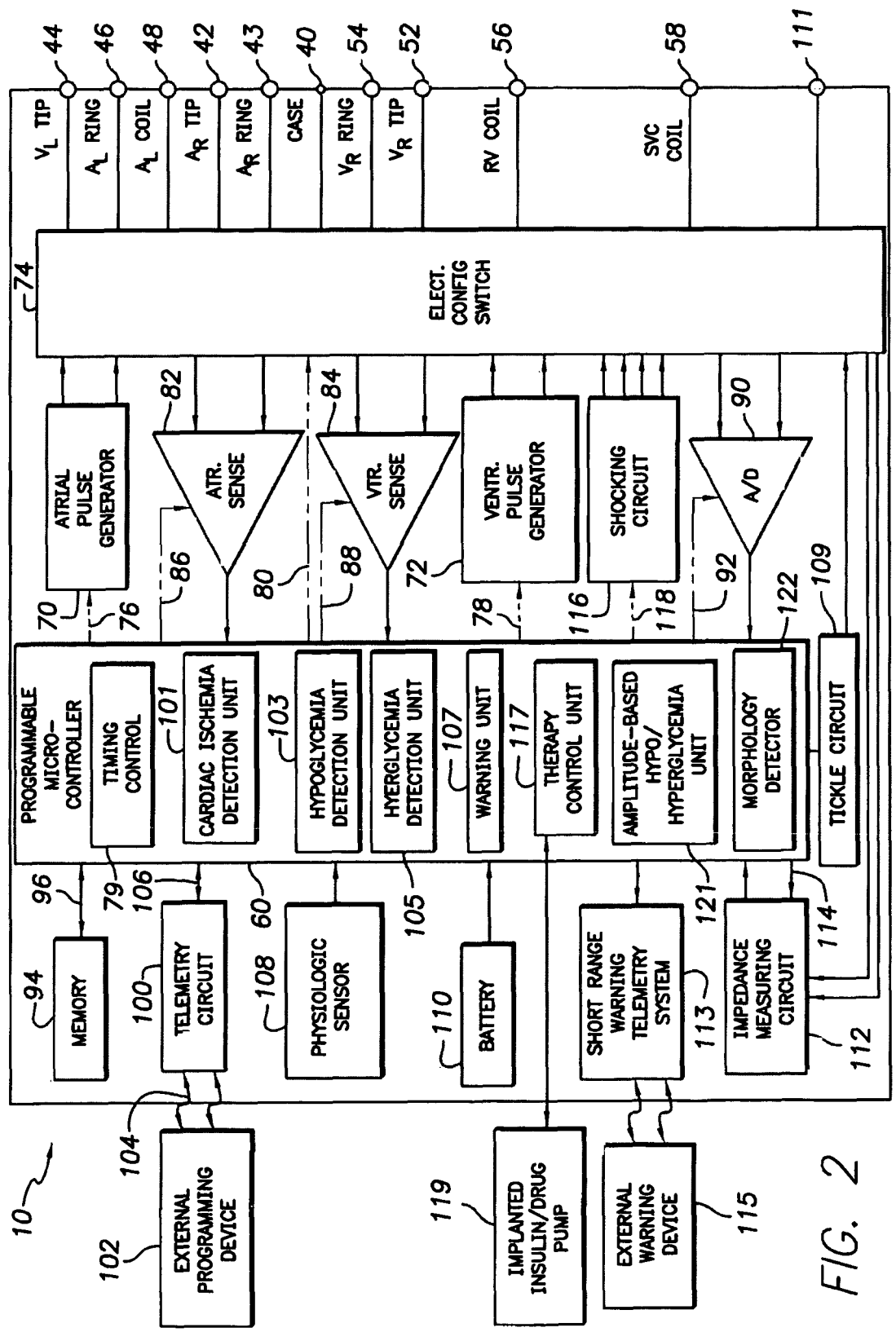
FIG. 2 is a functional block diagram of the implantable cardiac stimulation device of FIG. 1 illustrating basic elements of the stimulation device, and particularly illustrating components for detecting cardiac ischemia, hypoglycemia, and hyperglycemia based on various combinations of QTmax, QTend and STdeviation and other components for detecting and distinguishing hypoglycemia from hyperglycemia based on amplitudes of selected electrical events.
Figure 15:
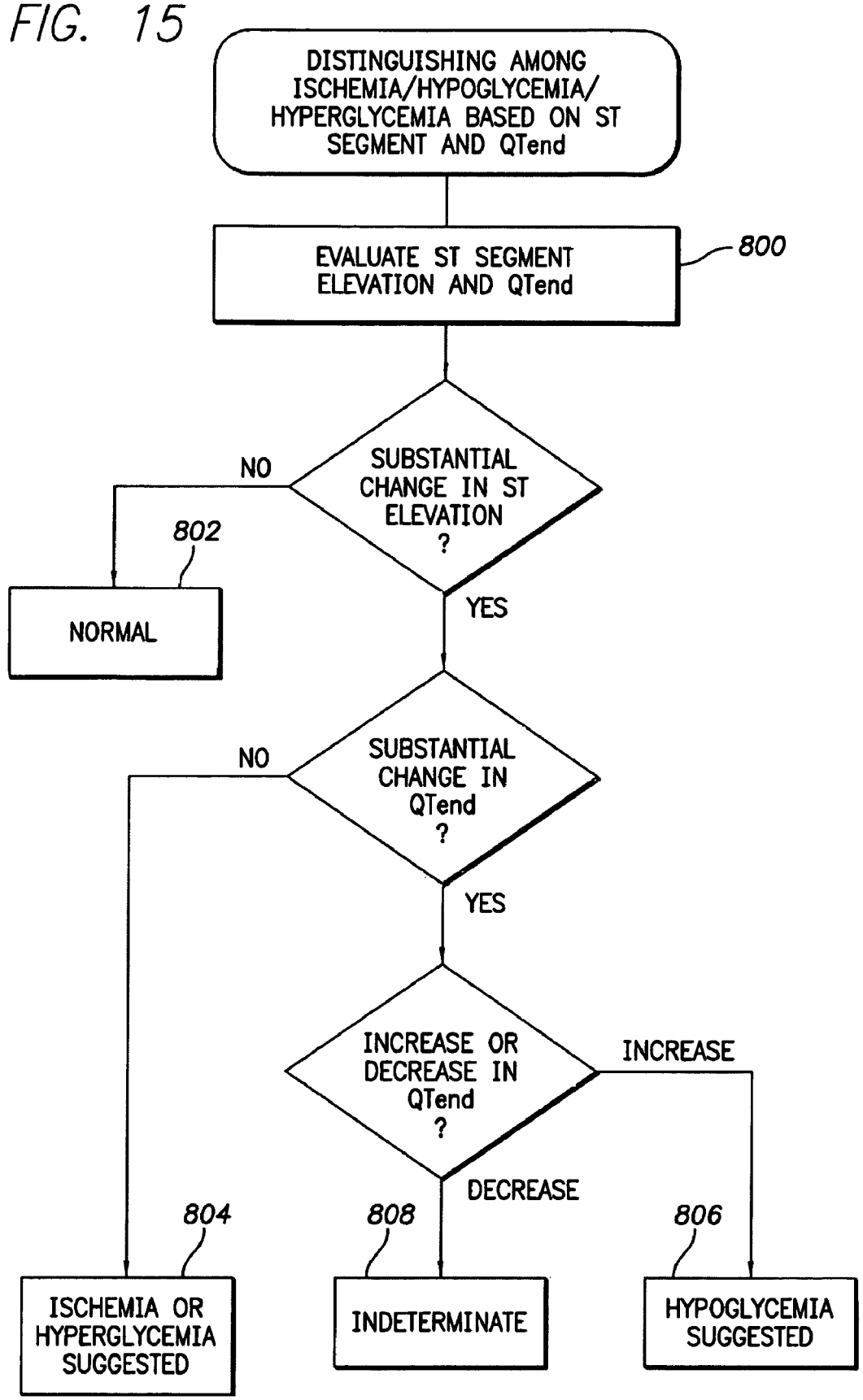
Figure 16:
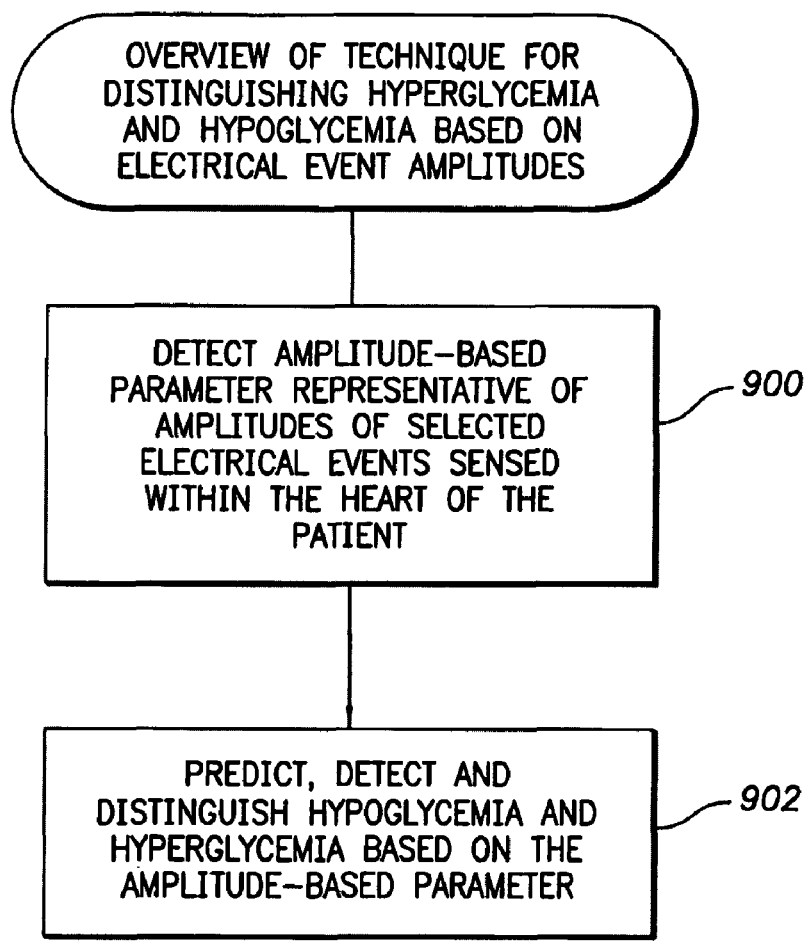
Figure 17:
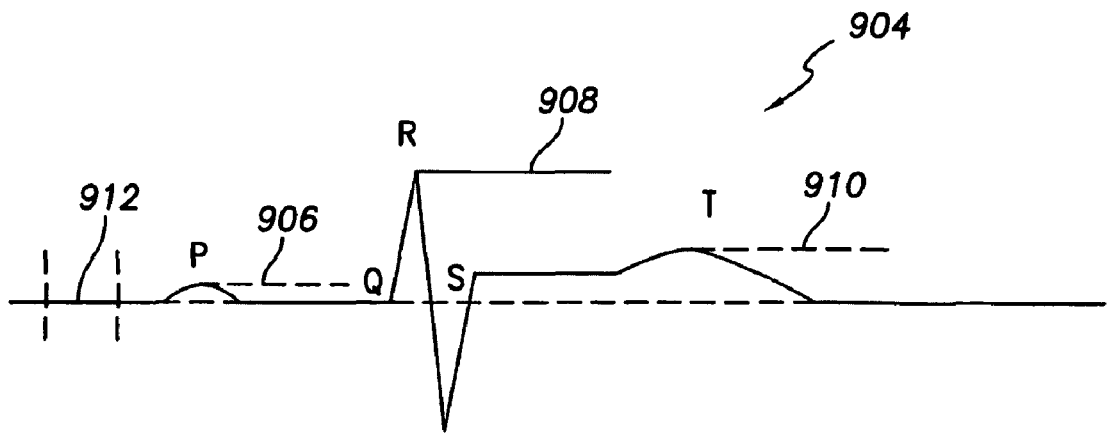
Figure 18:
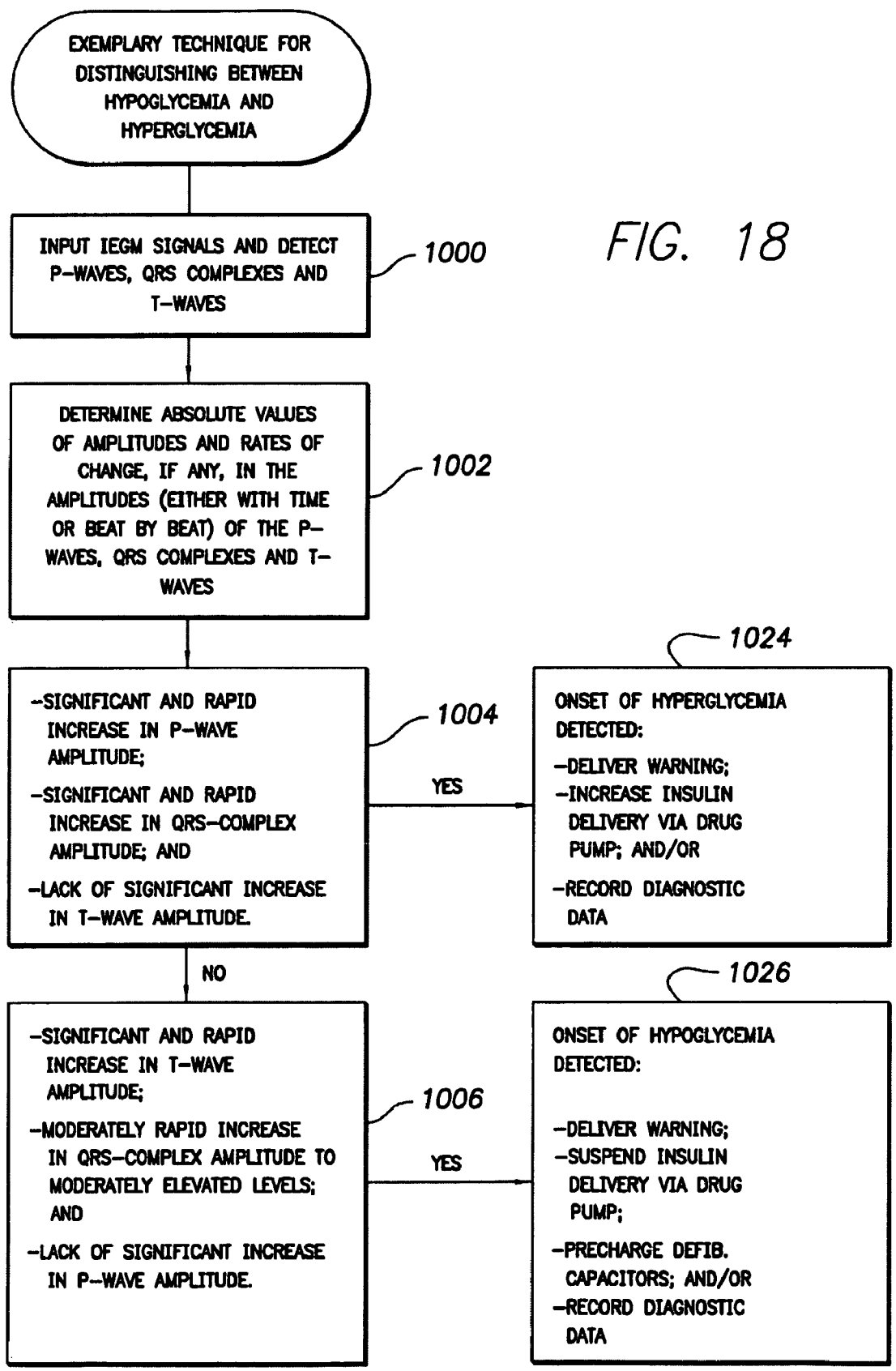
Figure 19:
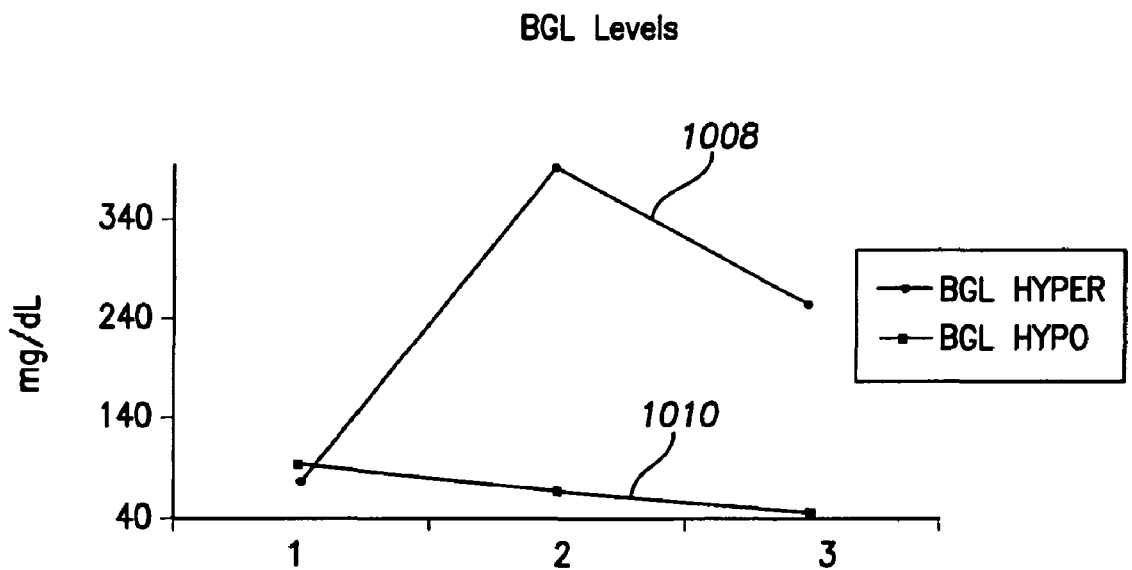
Figure 20:
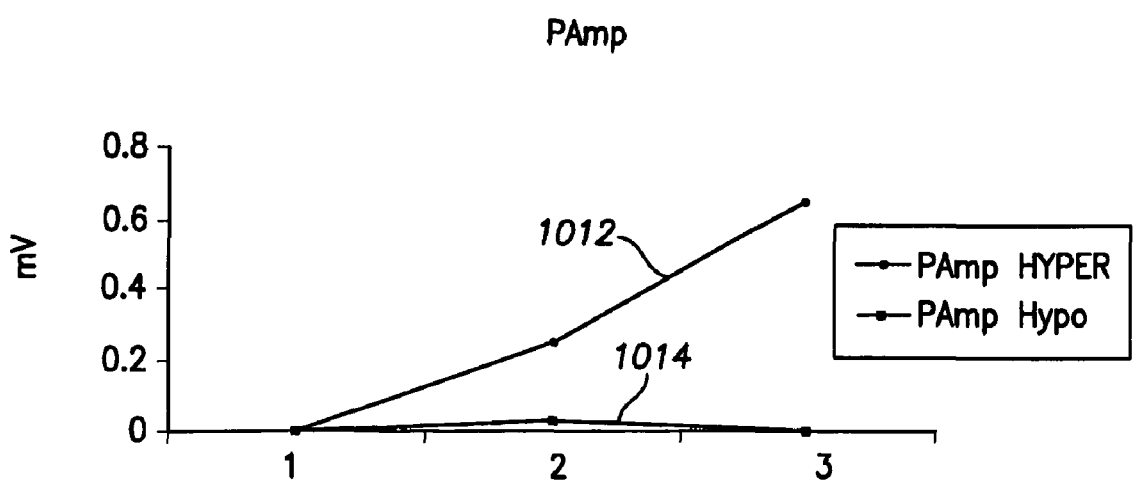
Figure 21:
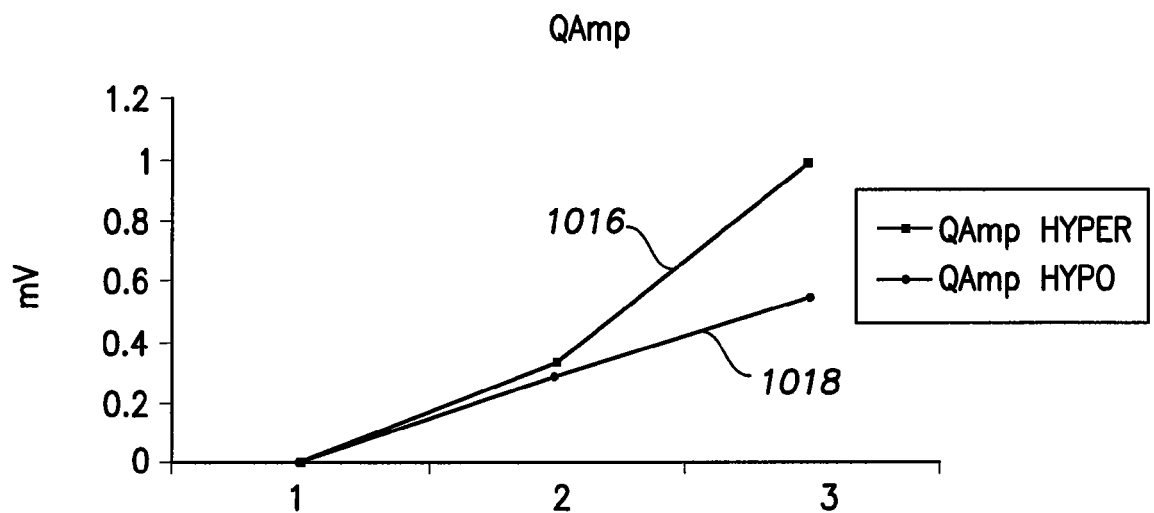
Figure 22:
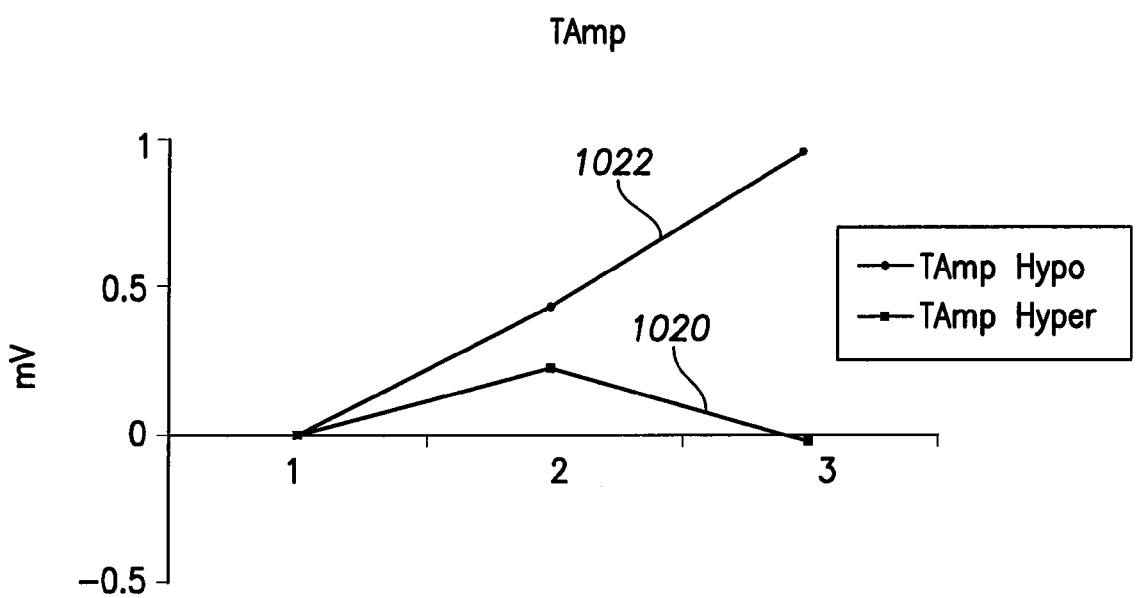

FIG. 15 is a flow chart providing an overview of an exemplary method performed by the implantable device of FIG. 2 for distinguishing among cardiac ischemia, hypoglycemia and hyperglycemia based on ST segment elevation and QTend;

FIG. 16 is a flow chart providing an overview of an exemplary method performed by the implantable device of FIG. 2 for detecting and distinguishing hypoglycemia from hyperglycemia based on amplitudes of selected electrical events;

FIG. 17 is a graph providing a stylized representation of the IEGM of a single heartbeat, particularly illustrating P-wave, QRS-complex and T-wave amplitudes;

FIG. 18 is a flow chart providing an overview of an exemplary method performed by the implantable device of FIG. 2 for detecting and distinguishing hypoglycemia and hyperglycemia based on based on P-wave, QRS-complex and T-wave amplitudes;

FIG. 19 is a graph illustrating changes in blood glucose levels associated with hyperglycemia and hypoglycemia;

FIG. 20 is a graph illustrating changes in P-wave amplitude associated with hyperglycemia and hypoglycemia;

FIG. 21 is a graph illustrating changes in QRS-complex amplitude associated with hyperglycemia and hypoglycemia; and FIG. 22 is a graph illustrating changes in T-wave amplitude associated with hyperglycemia and hypoglycemia.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
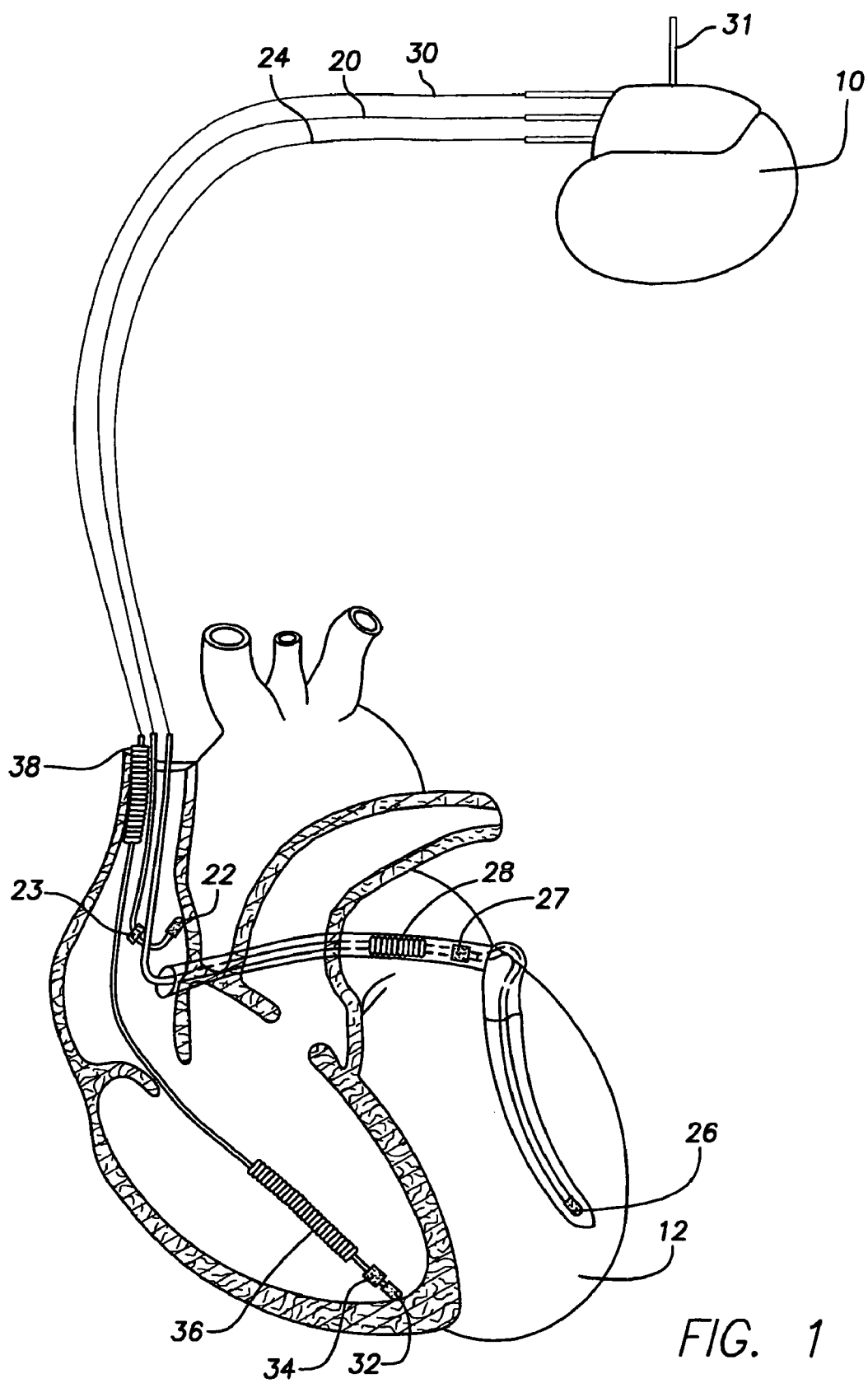
FIG. 1 is a simplified diagram illustrating an implantable stimulation device with at least three leads implanted in the heart of a patient for delivering multi-chamber stimulation and shock therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. To provide the "tickle warning" signal, an additional terminal 59 is provided for connection to the tickle warning electrode 31 of FIG. 1.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112, which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Further, with regard to FIG. 2, microcontroller 60 includes: a cardiac ischemia detection unit 101 for controlling the detection of episodes of cardiac ischemia; hypoglycemia detection unit 103 for controlling the detection of episodes of hypoglycemia; and a hyperglycemia detection unit 105 for controlling the detection of episodes of hyperglycemia. A warning unit 107 controls delivery of warning signals to the patient indicative of ischemia, hypoglycemia, or hyperglycemia. In particular, warning unit 107 controls a tickle circuit 109 that generates subcutaneous perceptible warning signals via lead 31 (FIG. 1), which is connected via connector 111. Device case electrodes 40 may be used as the return electrode for the tickle warning signal. Thereafter, warning unit 107 controls a short-range telemetry system 113 to transmit warning signals to an external handheld warning device 115 for confirmation. Additionally, a therapy control unit 117 may be provided to control therapy based upon the detection of ischemia, hypoglycemia or hyperglycemia. If an implantable drug 119 is provided, such as an insulin pump, the therapy control unit also controls delivery of insulin or other medications using the drug pump. The operation of components 101-119 is described below primarily with reference to FIGS. 1-15.

The microcontroller additionally includes an amplitude-based hypo/hyperglycemia unit 121 for predicting, detecting and/or distinguishing hypoglycemia from hyperglycemia based on the amplitudes of P-waves, QRS-complexes and T-waves, which is described below primarily with reference to FIGS. 16-22. The results of analysis performed by the hypo/hyperglycemia unit 121 may be exploited by detection units 101-105 to improve the specificity by which hypoglycemia, hyperglycemia and cardiac ischemia are detected, or the analysis may be exploited for any other advantageous purpose.

Referring now to the remaining figures, flow charts, graphs and other diagrams illustrate the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Cardiac Ischemia Detection Based on QTmax

Figure 3:
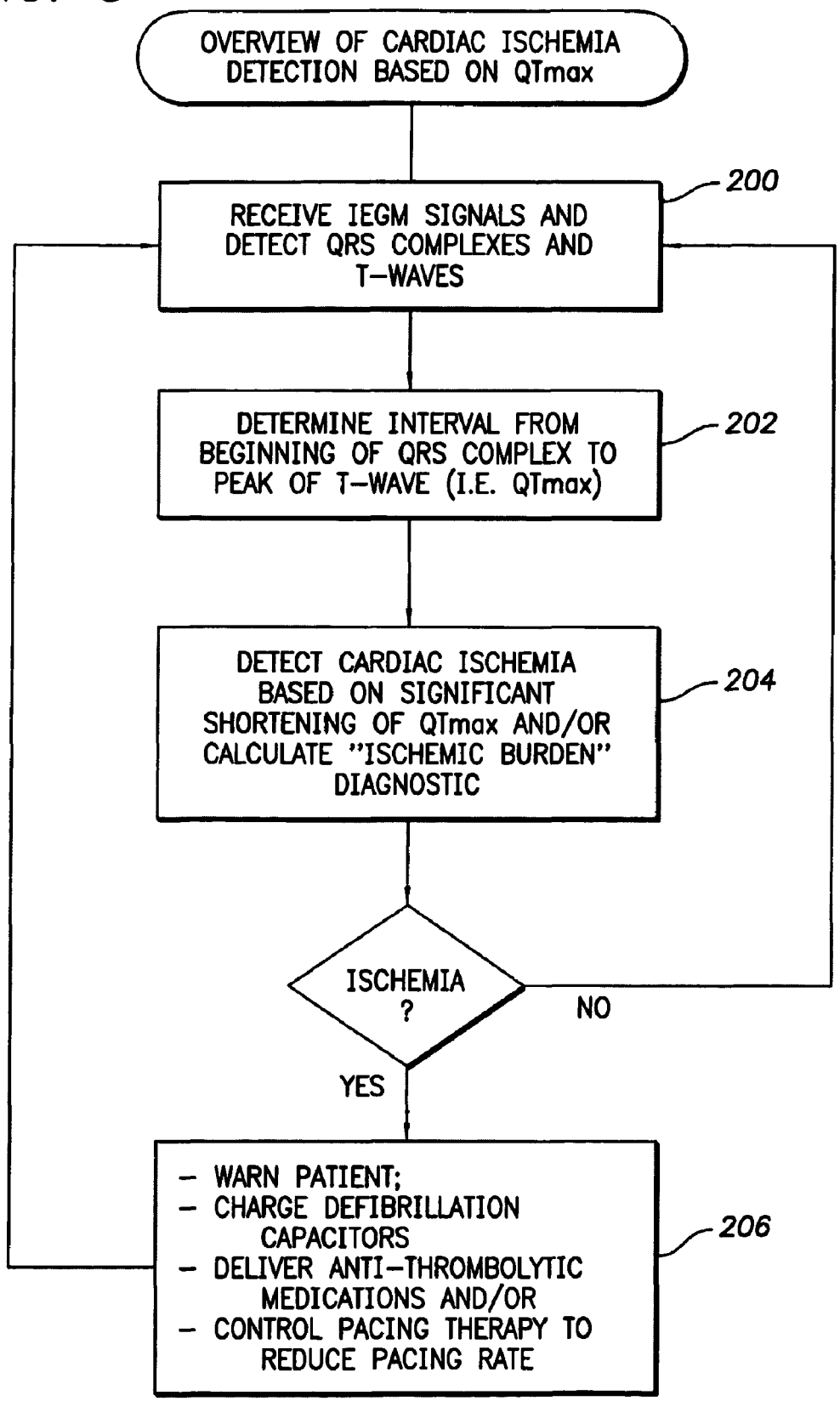
FIG. 3 is a flow chart providing an overview of an exemplary method performed by the device of FIG. 2 for detecting cardiac ischemia based on a reduction in QTmax.

FIG. 3 provides an overview of a QTmax-based cardiac ischemia detection technique performed by the device of FIG. 2. Initially, at step 200, IEGM signals are received and QRS-complexes and T-waves are identified therein. Then, the interval from the beginning of the QRS complex to the peak or maximum absolute amplitude of the T-wave is calculated, at step 202. This interval is referred to herein as QTmax. The Q wave of the QRS complex may be identified as the point within the QRS complex where the IEGM signal exceeds a threshold value set based on the maximum amplitude of the QRS complex itself. The maximum of the T-wave may be identified as the maximum point within a T-wave interval beginning 250 ms following the Q wave of the QRS complex and extending for 200 ms. These are merely exemplary values. At step 204, the onset of a cardiac ischemia is detected based upon detection of a significant shortening of QTmax. Routine experimentation may be performed to determine what constitutes "significant" insofar as changes in QTmax are concerned (and insofar as any other changes referred to herein as being significant are concerned.) In one example, a 10% or greater change in a given parameter is deemed to be significant. Note that QTmax values may be derived from either paced or sensed events but values derived from paced and sensed events should not be combined. In addition, QTmax varies with heart rate and so should be normalized based on heart rate. Bazettte's equation may be used for normalizing QTmax (and for normalizing other parameters discussed herein.)

Additionally, or in the alternative, at step 204, the device calculates an "ischemic burden" based on QTmax, which is representative of the proportion of the time ischemia is detected. In one example, the ischemic burden is a numerical value representative of the extent to and/or the time during which QTmax is shorter than its running average. Steps 200-204 are preferably performed once every 30 seconds.

So long as no ischemia is detected, steps 200-204 are merely repeated. If ischemia is detected, however, the patient is warned of the ischemia by application of an internal perceptible "tickle" notification signal, at step 206. If the device is configured to generate warning signals for other conditions, such as hyperglycemia or hypoglycemia, the device preferably employs different notification signal frequencies for the different warnings so that the patient can properly distinguish between different warnings. In addition, warning signals may be transmitted using a short-range telemetry system to a handheld warning device using techniques described within the above-referenced patent application to Wang et al. The handheld warning device thereby provides confirmation of the warning to the patient, who may be otherwise uncertain as to the reason for the internally generated tickle warning signal. Additionally, if so equipped, the device may automatically control therapy in response to the ischemia. For example, if a drug pump is implanted within the patient, the pump may be controlled to deliver suitable anti-thrombolytic medications directly to the patient. Implantable devices for delivering anti-thrombolytic drugs are discussed in U.S. Pat. No. 5,960,797 to Kramer, et al. The device may also change pacing parameters in response to the detection of ischemia to, for example, deactivate overdrive pacing, which may exacerbate the ischemia. Other forms of elevated pacing may be discontinued as well, such as AF suppression therapy or activity-based rate responsive pacing. Various techniques for controlling delivery of therapy in response to ischemia are discussed U.S. Pat. No. 6,256,538 to Ekwall, listed above. See also U.S. Pat. No. 6,377,852 to Bornzin et al. which provides techniques for slowing the heart rate in response to ischemia. In addition, if the device is an ICD, then it may be controlled to immediately begin charging defibrillation capacitors in expectation of delivery of a defibrillation shock, which may be needed if the ischemia triggers VF.

Hence, FIG. 3 provides an overview of technique that seeks to detect the onset of cardiac ischemia based primarily on changes in QTmax. As will be explained below, additional parameters of the IEGM signal, such as STdeviation, may be employed to confirm the detection made based upon to QTmax. Insofar as the detection of T-waves at step 200 is concerned, the invention may exploit techniques set forth in the aforementioned Patent Application of Kroll (Serial Number 2004/0077962). Certain techniques described therein are particularly well suited for detecting T-waves with a high degree of accuracy to permit precise detection of features of the T-wave (such as its peak) so as to achieve more precise measurement of QRS/T-wave intervals. The patent application to Kroll is fully incorporated by reference herein. The invention also may exploit T-wave detection techniques set forth within the aforementioned patent application to Min et al., which help prevent P-waves from being misinterpreted as T-waves on unipolar sensing channels.

Figure 4:
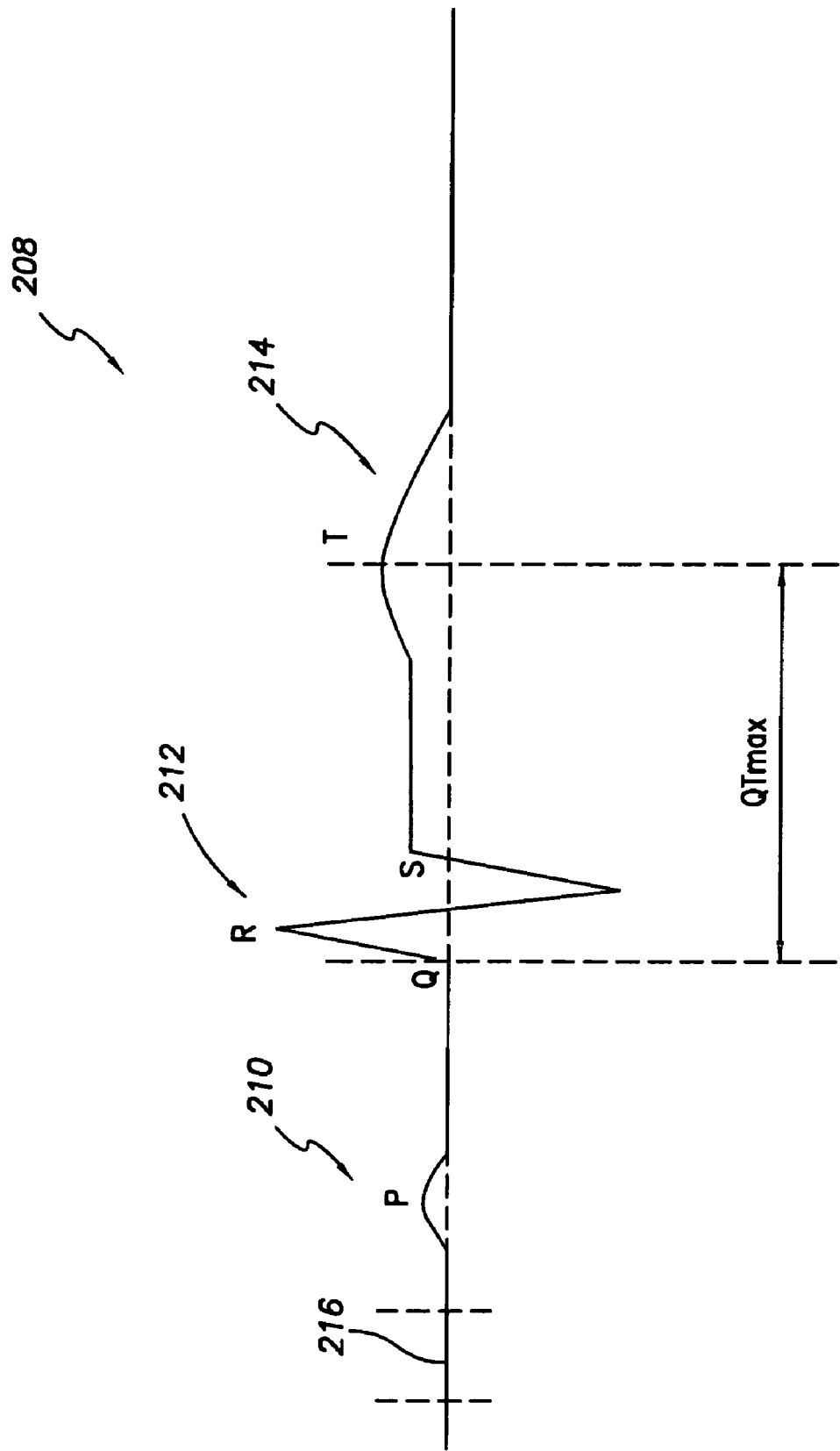
FIG. 4 is a graph providing a stylized representation of the IEGM of a single heartbeat, particularly illustrating the QTmax interval.

FIG. 4 illustrates the QTmax interval. Briefly, the figure provides a stylized representation of an exemplary IEGM trace 208 for a single heartbeat for a patient suffering myocardial ischemia. The stylized representation of the IEGM signal of FIG. 4 is provided for illustrative purposes and should not be construed as an actual, clinically detected IEGM signal. The heartbeat includes a P-wave 210 representative of an atrial depolarization, a QRS complex 212 representative of a ventricular depolarization and a T-wave 214 representative of ventricular repolarization. The QRS complex itself is defined by points Q, R, and S. Q represents the beginning of the complex; R represents the peak of the complex; and S represents the end of the complex. In the examples described and illustrated herein, the aforementioned QTmax interval is specified as the time interval from point Q to the peak or maximum amplitude point of T-wave. However, QTmax may alternatively be calculated based on other points or features of the QRS complex, such as the R point or the S point of the complex, so long as the calculations are consistent. As it is used herein, the "Q" of QTmax generally refers to the QRS complex and not specifically to the Q point of the QRS complex. Hence, the term QTmax encompasses RTmax as one example and STmax as another example. Also, in the particular example of FIG. 4, the peak of the T-wave is positive, i.e. it is greater than a baseline voltage of the IEGM signal. This need not be the case. In other examples, the peak has a negative value with respect to a baseline of the IEGM signal. The polarity of the entire signal may also be reversed. Herein, the peak or maximum amplitude of T-wave refers to the peak or maximum of the absolute value of the difference between the T-wave voltage and the baseline voltage of the IEGM signal. The baseline voltage 216 may be measured during an interval prior to the P-wave, as shown. The interval may be, for example, 50 milliseconds (ms) in duration, beginning 100 ms prior to the P-wave. Alternatively, the interval may be timed relative to the QRS complex. If timed relative to the QRS complex, the interval may commence 250 ms prior to the R wave of the QRS complex. Also alternatively, a single detection point may be used, rather than a detection interval.

Figure 5:
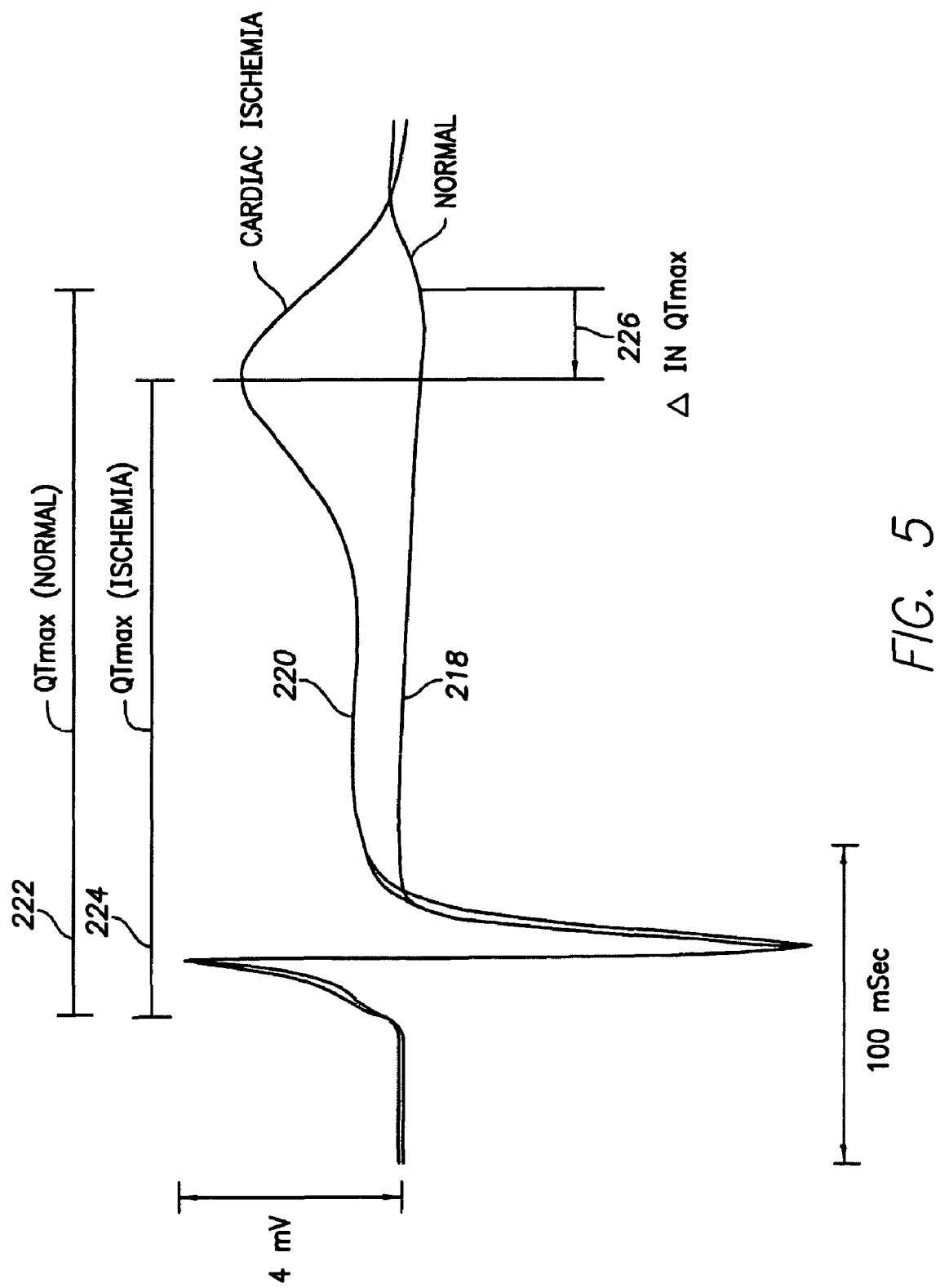
FIG. 5 is a graph providing exemplary representations of the IEGM of a single heart beat, particularly illustrating a reduction in the QTmax interval caused by cardiac ischemia.

FIG. 5 illustrates change in QTmax brought on by acute myocardial ischemia. A first exemplary IEGM trace 218 represents a heartbeat of healthy patient, i.e. one not subject to cardiac ischemia, hypoglycemia or hyperglycemia. A second trace 220 illustrates the heartbeat for a patient suffering an acute myocardial ischemia. The traces are IEGM signals derived from voltage differences between the tip of a right ventricular (RV) lead and the device case. Note first that the IEGM trace for the healthy patient exhibits a T-wave that is reversed in polarity with respect to T-wave of the patient suffering the ischemia. T-wave inversion is typical during ischemia as well as during other conditions such as electrolyte abnormalities, which influence repolarization. Therefore, FIG. 5 illustrates that the QTmax feature is valid even in the presence of a T-wave inversion. In any case, for the purposes of ischemia detection, the peak of the T-wave during ischemia occurs earlier than the corresponding peak without ischemia. In other words, QTmax during ischemia 222 is shorter than QTmax without ischemia 224. Hence, a large positive value of $\Delta$QTmax (226) is observed, where $\Delta$QTmax represents the amount of the reduction in QTmax. A negative value of $\Delta$QTmax is associated with an increase in interval length. In the example FIG. 5, $\Delta$QTmax is represented as a positive number. Note that significant negative $\Delta$QTmax intervals may also be observed which, as will be explained below, are instead indicative of hypoglycemia.

$\Delta$QTmax is the value used to detect the onset of ischemia. Preferably, any change in QTmax from a current baseline value is tracked. In one example, the device tracks a running average of QTmax intervals (derived from sensed events and normalized based on heart rate) for use as a baseline value. Different baseline values may be calculated for different heart rate ranges. In any case, for each new heartbeat, the device compares the QTmax interval for that heartbeat against the appropriate baseline to calculate ΔQTmax for that heartbeat. ΔQTmax values are averaged over, e.g., eight to sixteen heartbeats and then compared against a predetermined QTmax-based threshold. If the average exceeds the threshold, cardiac ischemia is thereby indicated. The threshold is a programmable value set, for example, based upon a percentage of the running average of the QTmax interval. In one specific example, if ΔQTmax is a positive value, which exceeds 10% of the running average of the QTmax intervals, cardiac ischemia is thereby indicated (i.e. QTmax has been found to be reduced by 10%). Otherwise conventional threshold comparison techniques may be employed for use with ΔQTmax. In another example, rather than comparing an average based on eight to sixteen values to the threshold, the occurrence of only a single ΔQTmax value exceeding the threshold is indicative of ischemia. In yet another example, if ΔQTmax exceeds the threshold for three out of five heartbeats, ischemia is indicated. Multiple thresholds may be defined, if desired, to trigger warning signals indicative of different levels of urgency. For example, if ΔQTmax exceeds a first, lower threshold, a warning signal indicative of a moderate ischemia is issued. If ΔQTmax exceeds a higher threshold, a second warning signal indicative of a more serious ischemia is issued. As can be appreciated, a wide variety of specific implementations may be provided in accordance with the general techniques described herein. Routine experimentation may be performed to determine appropriate threshold levels.

Hence, FIGS. 3-5 provide an overview of techniques for detecting the onset of cardiac ischemia based on changes in the QTmax interval. As will be explained below, particularly with reference to FIG. 13, STdeviation may be used to corroborate any cardiac ischemia detection made based upon QTmax intervals. Other parameters may be used as well to corroborate the detection of cardiac ischemia, including post T-wave-based detection parameters described in the above-referenced patent application to Wang et al. and T-wave energy-based parameters and T-wave slope-based parameters described in the above-referenced patent application Min et al.

Cardiac Ischemia Detection Based on STdeviation and QTend

Figure 6:
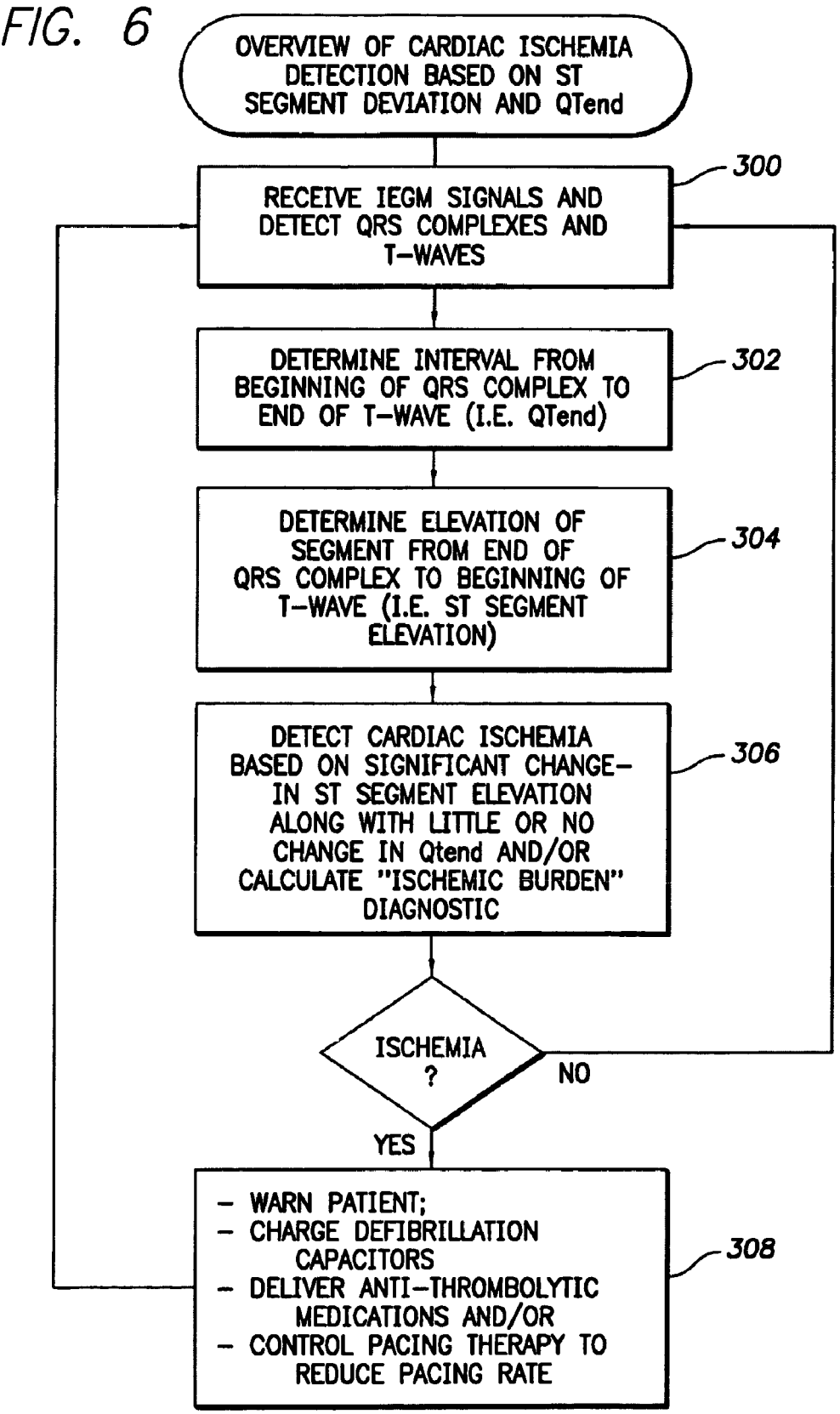
FIG. 6 is a flow chart providing an overview of an exemplary method performed by the device of FIG. 2 for detecting cardiac ischemia based primarily on a significant deviation in the ST segment along with little or no change in the QTend interval.

FIG. 6 provides an overview of a QTend-based cardiac ischemia detection technique performed by the device of FIG. 2. Many aspects of the technique are similar to those of the technique of FIG. 3 and will not be described again in detail. Initially, at step 300, IEGM signals are received and QRS-complexes and T-waves are identified therein. Then, the interval from the beginning of the QRS complex to the end of the T-wave is calculated, at step 302. This interval is referred to herein as QTend. In the examples described and illustrated herein, the QTend interval is specified as the time interval from point Q of the QRS complex to the end point of the T-wave. However, as with QTmax, QTend may alternatively be calculated based on other points or features of the QRS complex, such as the R point or the S point of the complex, so long as the calculations are consistent. The elevation of the interval from the end of the QRS complex to the beginning of the T-wave is also calculated, at step 304. This interval is referred to herein as the ST segment, its elevation is referred to as the ST elevation, and changes in the ST elevation is the STdeviation. Otherwise conventional techniques for detecting ST segment elevation may be used. Detection of ST segment elevation is discussed, for example, in U.S. Pat. Nos. 6,016,443 and 6,256,538 to Ekwall, listed above. At step 306, the onset of a cardiac ischemia is detected based upon observation of a significant deviation in the ST segment along with little or no change in QTend. A deviation in the ST is preferably calculated as a change in the average amplitude of the ST segment. Since the polarity of the IEGM signal is arbitrary, this may, in some cases, represent an increase in voltage of the ST segment and in other cases a decrease in voltage. It is the change in ST segment elevation that is important. As before, data from paced and sensed events should not be combined. QTend values should be normalized based on heart rate. Moreover, ST segments may be referenced beat-by-beat to either the PQ or TP regions of the IEGM.

Additionally, or in the alternative, at step 304, the device calculates an ischemic burden based on STdeviation and QTend, which is representative of the risk of ischemia. In one example, the ischemic burden is a single metric value derived from STdeviation and changes in QTend. Techniques for combining different parameters into a single metric value are set forth in U.S. Patent Application 2004/0138716, to Koh et al., entitled "System and Method for Detecting Circadian States Using an Implantable Medical Device", published Jul. 15, 2004. If QTend and STdeviation are measured for diagnostic purposes only, steps 300-306 are preferably performed once an hour to calculated and record the ischemic burden. If measured for detecting ischemia, steps 300-306 are preferably performed more often, e.g. once every 30 seconds. In any case, so long as no ischemia is detected, steps 300-306 are merely repeated. If ischemia is detected, however, the patient is warned of the ischemia, at step 308, and, if so equipped, the device automatically controls therapy in response to the ischemia. If the device is an ICD, it may be controlled to immediately begin charging defibrillation capacitors.

Figure 7:
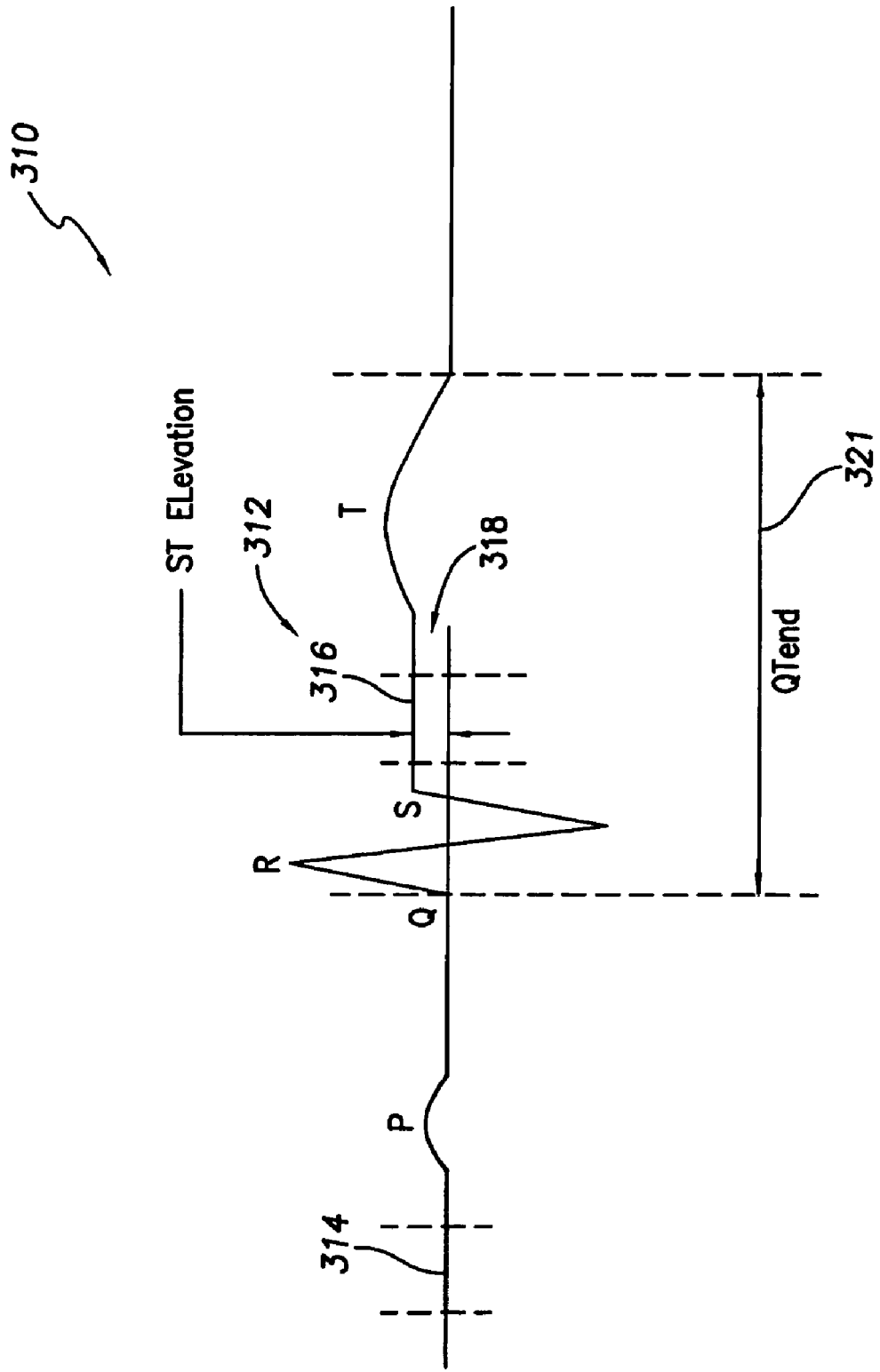
FIG. 7 is a graph providing a stylized representation of the IEGM of a single heartbeat, particularly illustrating STdeviation and the QTend interval.

Hence, FIG. 6 provides an overview of technique that seeks to detect the onset of cardiac ischemia based on a combination of STdeviation and QTend. Additional parameters of the IEGM signal, such as the aforementioned QTmax interval, may be employed to confirm the detection. FIG. 7 illustrates ST segment elevation and the QTend interval. Briefly, FIG. 7 provides a stylized representation of an exemplary IEGM trace 310 for a single heartbeat for a patient suffering a myocardial ischemia. The ST segment 312 is the interval from the end of the QRS complex to the start of the T-wave. The duration of this interval is not of interest in this technique. However, its deviation, i.e. the extent to which its elevation changes over time is of interest. To calculate the elevation of an individual ST segment deviation, the device identifies a window 316 with the ST segment. The elevation of the ST segment (relative to a baseline voltage) within the window is denoted by reference numeral 318. The ST segment elevation may be measured during a specified interval following the QRS complex, as shown. The interval may be, for example, 50 ms in duration, beginning 50 ms following the R wave of the QRS complex. For ventricular paced events, the interval may begin, for example, 80 ms following a V-pulse and extend for 50 ms. These are merely exemplary values. The elevation may be quantified based on the mean of the ST segment sample. Meanwhile, the QTend interval is the time interval between the beginning of the QRS complex and the end point of the T-wave, i.e. the point at which the slope of the T-wave following its peak becomes substantially flat. Techniques for detecting T-wave slope are set forth in the aforementioned patent application to Min et al. The QTend interval is denoted by reference numeral 321.

Figure 8:
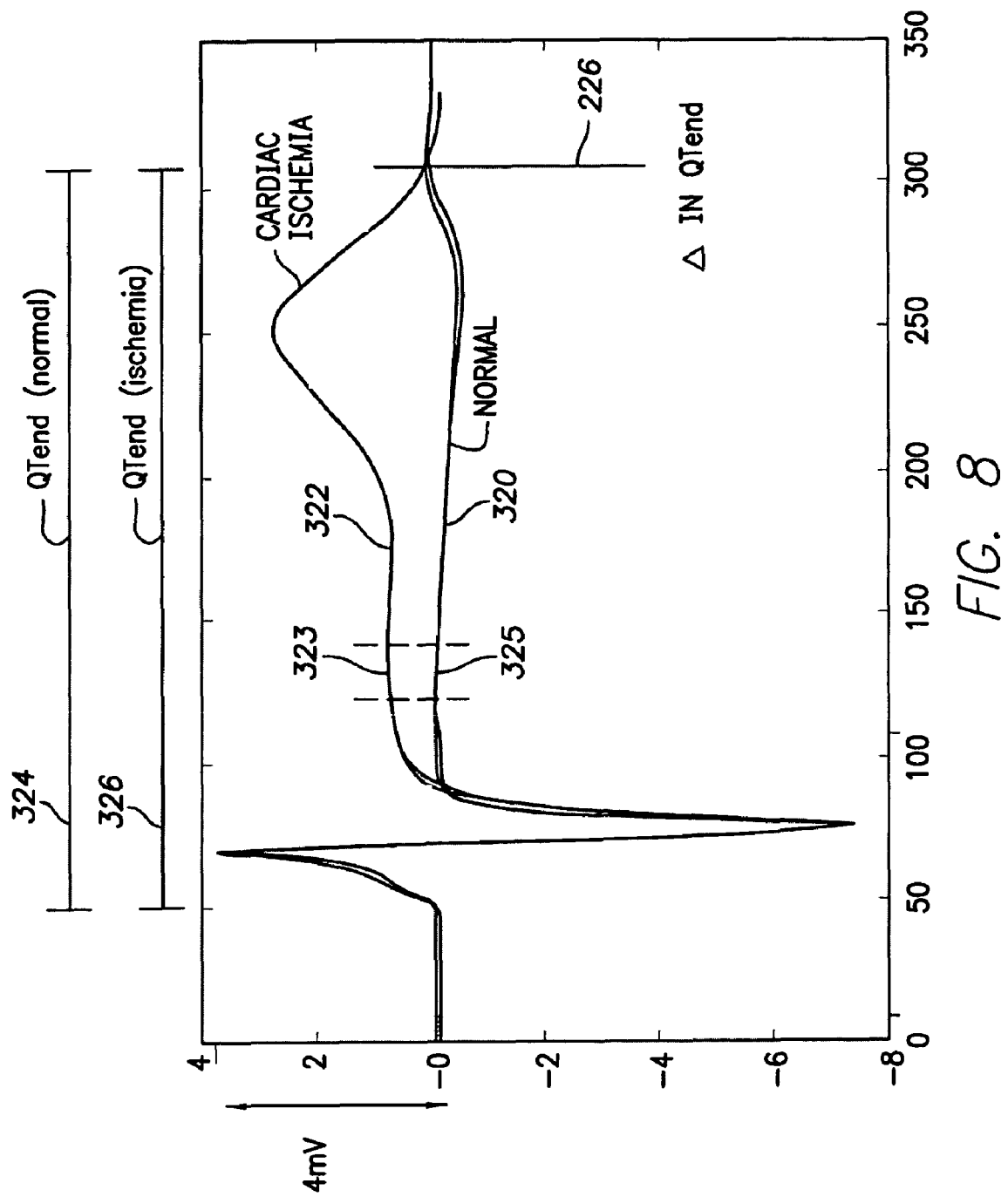
FIG. 8 is a graph providing exemplary representations of the IEGM of a single heart beat, particularly illustrating a significant deviation in the ST segment caused by cardiac ischemia, along with a lack of change in QTend.

FIG. 8 illustrates changes in ST segment elevation brought on by acute myocardial ischemia. A first exemplary IEGM trace 320 represents a heartbeat of a healthy patient, i.e. one not subject to cardiac ischemia or hypo/hyperglycemia. A second trace 322 illustrates the heartbeat for a patient suffering an acute myocardial ischemia. As with other traces illustrated herein, the IEGM signals of FIG. 8 are exemplary representations of IEGM signals provided for illustrative purposes only. Comparing the two traces, the elevation of the ST-segment during ischemia (323) is much greater than the elevation of the ST-segment without ischemia (325), i.e. there is a significant STdeviation. However, there is little or no change in QTend, i.e. the absolute value of ΔQTend is substantially zero, where ΔQTend represents the amount of the reduction, if any, in QTend interval duration. (A positive value of ΔQTmax is associated with a decrease in interval length. A negative value of ΔQTmax is associated with an increase in interval length. For the purposes of the technique of FIG. 6, only the magnitude of any change in QTend is important.) Hence, QTend helps corroborate the detection of ischemia made based on STdeviation. In particular, as will be explained in more detail below with reference to FIGS. 9-10, a change in ST segment elevation brought on by hypoglycemia will additionally trigger a significant increase in QTend. Hence, without an examination of QTend, it may not be possible to reliably distinguish a change in ST segment elevation caused by ischemia from a change caused by hypoglycemia.

Preferably, any changes in the ST segment elevation and in QTend from current baseline values are tracked. In one example, the device tracks a running average of the ST segment elevation (as derived from sensed events) and then, for each new heartbeat, the device compares the ST segment elevation for that heartbeat against the running average to calculate an STdeviation value for that heartbeat. Note that ST segment values need not be normalized based on heart rate. The device also tracks a running average of the QTend interval (as derived from sensed events and normalized based on heart rate) and then, for each new heartbeat, compares the QTend interval for that heartbeat against the running average to calculate a ΔQTend value for that heartbeat. The value of STdeviation for the heartbeat is averaged over, e.g., eight to sixteen heartbeats and compared against a predetermined deviation-based threshold. If the average exceeds the threshold, then the absolute value of ΔQTend is also averaged over eight to sixteen heartbeats and compared against a predetermined ΔQTend-based threshold. If STdeviation exceeds its respective threshold (indicating a significant change in ST segment elevation), but the absolute value of ΔQTend does not exceed its respective threshold (indicating little or no change in QTend), then cardiac ischemia is thereby indicated. (If STdeviation exceeds its respective threshold and the absolute value of ΔQTend also exceeds its respective threshold, an indication of hypoglycemia may instead be provided. See FIG. 13, discussed below.)

The various thresholds are programmable values set, for example, based upon respective running averages. In one specific example, the threshold for ΔQTend is set to 10% of the running average of the QTend intervals. The threshold for STdeviation may be set, for example, based on some percentage (e.g. 20%) of a running average of peak-to-peak voltage swings in QRS complexes, i.e. based on a percentage of the average difference from a maximum positive voltage to a maximum negative voltage within each QRS complex. Alternatively, the threshold for STdeviation may be set to a preset voltage difference, such as 0.25-0.5 milli-Volts (mV). As with the QTmax-based technique, alternative threshold comparison techniques may instead be used. Multiple thresholds may be defined, in some implementations, to trigger warning signals indicative of different levels of urgency. Routine experimentation may be performed to determine appropriate threshold levels.

Hence, FIGS. 6-8 provide an overview of techniques for detecting the onset of cardiac ischemia based on an examination of ST segment deviation in conjunction with QTend interval. Other parameters may be used to further corroborate the detection of cardiac ischemia, such as the QTmax interval and parameters described in the above-referenced patent applications to Wang et al. and Min et al. In the next section, techniques for detecting hypoglycemia will be described.

Hypoglycemia Detection Based on QTmax and/or QTend

Figure 9:
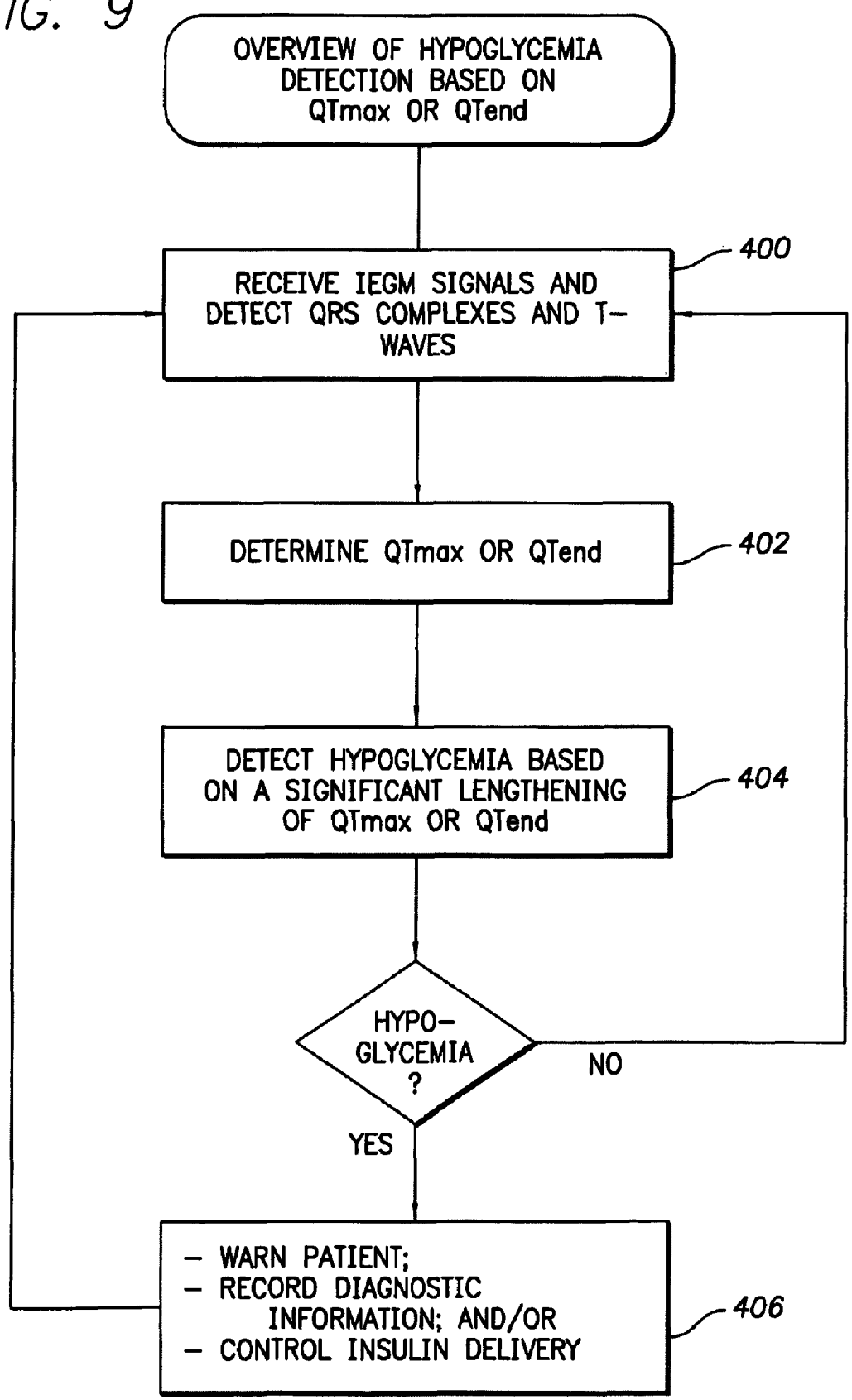
FIG. 9 is a flow chart providing an overview of an exemplary method performed by a hypoglycemia detection system of FIG. 2 for detecting hypoglycemia based primarily on a significant lengthening of either QTmax or QTend.

FIG. 9 provides an overview of hypoglycemia detection techniques performed by the device of FIG. 2. Many aspects of this technique are similar to those of the ischemia detection techniques described above and will not be described again in detail. Initially, at step 400, IEGM signals are received and QRS-complexes and T-waves are identified therein. Then, at step 402, QTmax and QTend intervals are measured. At step 404, the onset of hypoglycemia is detected based upon observation of a significant lengthening of either QTend or QTmax or both. In this regard, both QTmax and QTend increase due to hypoglycemia. Hence, one or the other is sufficient to detect hypoglycemia. Both are preferred to enhance detection reliability. A change in ST segment elevation may be used to further corroborate the detection (see FIG. 13). As before, data from paced or sensed events should not be combined. QTmax and QTend intervals should be normalized based on heart rate.

Figure 10:
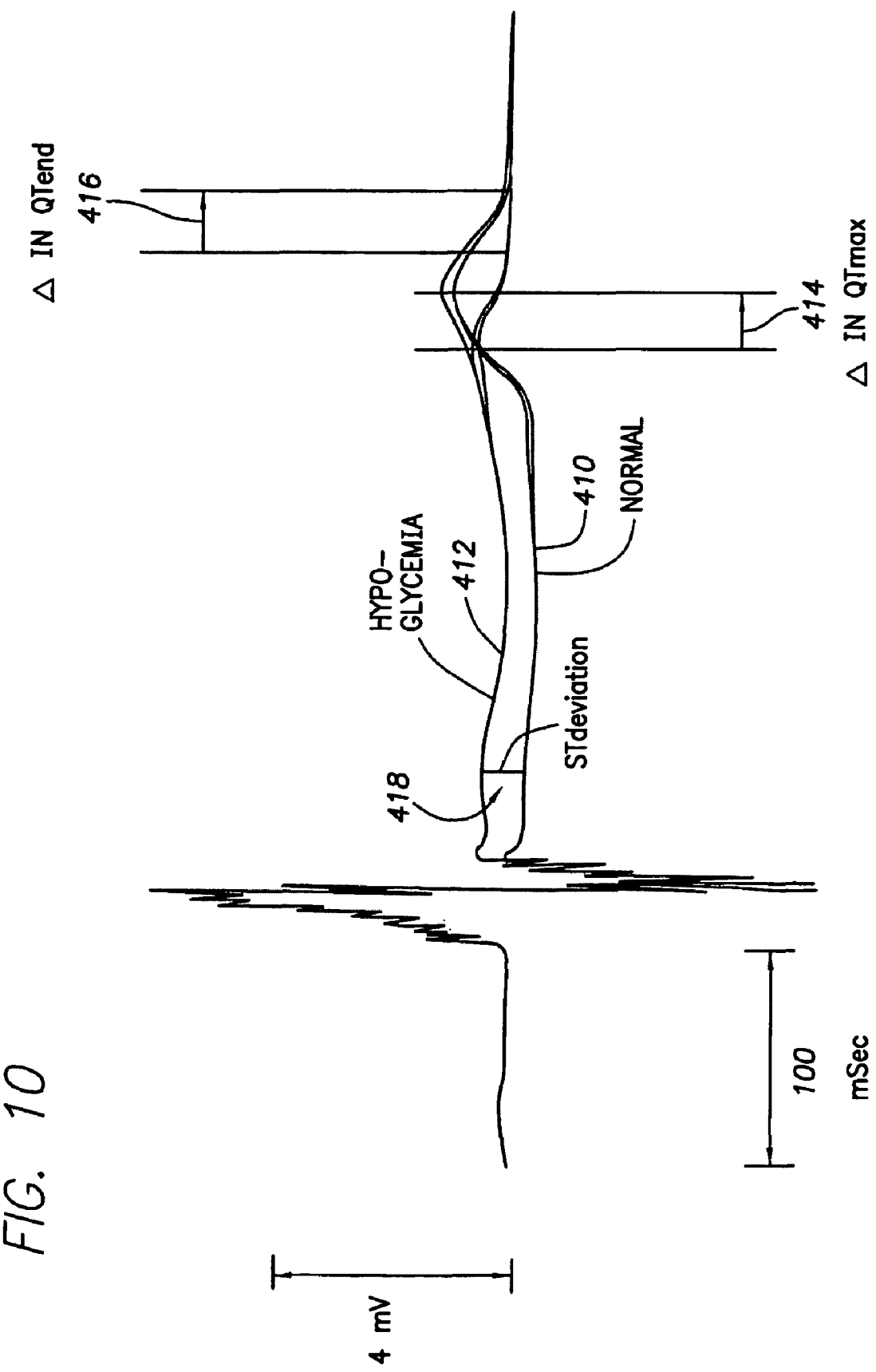
FIG. 10 is a graph providing exemplary representations of the IEGM of a single heartbeat, particularly illustrating a significant lengthening of both QTmax and QTend.

Additionally, or in the alternative, STdeviation, QTmax and QTend may be stored for diagnostic purposes. The device may calculate a single value representative of the risk of hypoglycemia based on a combination of STdeviation, QTmax and QTend, similar to the ischemic burden discussed above. In any case, so long as hypoglycemia is not detected, steps 400-404 are merely repeated. If hypoglycemia is detected, however, the patient is warned, at step 406. Preferably, the warning signal differs from the one generated for ischemia. If so equipped, the device may automatically initiate therapy appropriate for responding to hypoglycemia. For example, if an insulin pump is implanted within a diabetic patient, the pump may be controlled to adjust the dosage of insulin in response to hypoglycemia. Techniques for controlling delivery of therapy in response to hypoglycemia are set forth in the Patent Application of Kroll, incorporated by reference above. Information regarding implantable insulin pumps may be found in U.S. Pat. No. 4,731,051 to Fischell and in U.S. Pat. No. 4,947,845 to Davis. Hence, FIG. 9 provides an overview of technique that seeks to detect the onset of hypoglycemia based on a lengthening of QTmax or QTend. FIG. 10 illustrates QTmax and QTend brought on by hypoglycemia, as well as changes in ST segment elevation. A first exemplary IEGM trace 410 represents a heartbeat of a healthy patient, i.e. one not subject to hypo/hyperglycemia or cardiac ischemia. A second trace 412 illustrates the heartbeat for a patient suffering from hypoglycemia. As with other traces illustrated herein, the IEGM signals of FIG. 10 are exemplary representations of IEGM signals provided for illustrative purposes only. Comparing the two traces, there is a significant lengthening of both QTmax and QTend, i.e. both ΔQTmax and ΔQTend are large in magnitude. (As explained above, ΔQTmax and ΔQTend are defined as positive numbers for a reduction in interval length and as negative numbers for an increase in interval length.)

Hence, an increase in either QTmax or QTend or both allows the device to detect hypoglycemia. STdeviation may be used to corroborate the determination. As can be seen from FIG. 10, the elevation of the ST segment changes in response to hypoglycemia. Preferably, any changes in QTmax and/or QTend are measured with respect to baseline values of those parameters. In one example, the device tracks running averages QTmax and QTend (as derived from sensed events and normalized based on heart rate) from use as baseline values. Different baseline values may be calculated for different heart rate ranges. Then for each new heartbeat, the device compares new values for those parameters against the appropriate baseline values to calculate ΔQTmax and ΔQTend values for that heartbeat. In the example, the ΔQTmax and ΔQTend values are averaged over eight to sixteen heartbeats. ΔQTmax is compared against a predetermined ΔQTmax-based threshold and ΔQTend is compared against a predetermined ΔQTend-based threshold and. These thresholds may differ in value from the corresponding thresholds discussed above. If ΔQTmax and ΔQTend both exceed their respective thresholds, an indication of hypoglycemia is thereby provided. The various thresholds are programmable values set, for example, based upon percentages of running averages of the respective interval. Again, multiple thresholds may be defined, if desired, to trigger warning signals indicative of different levels of urgency. Routine experimentation may be performed to determine appropriate threshold levels. In the next section, techniques for instead detecting hyperglycemia will be described.

Hyperglycemia Detection Based on STdeviation, QTmax and QTend

Figure 11:
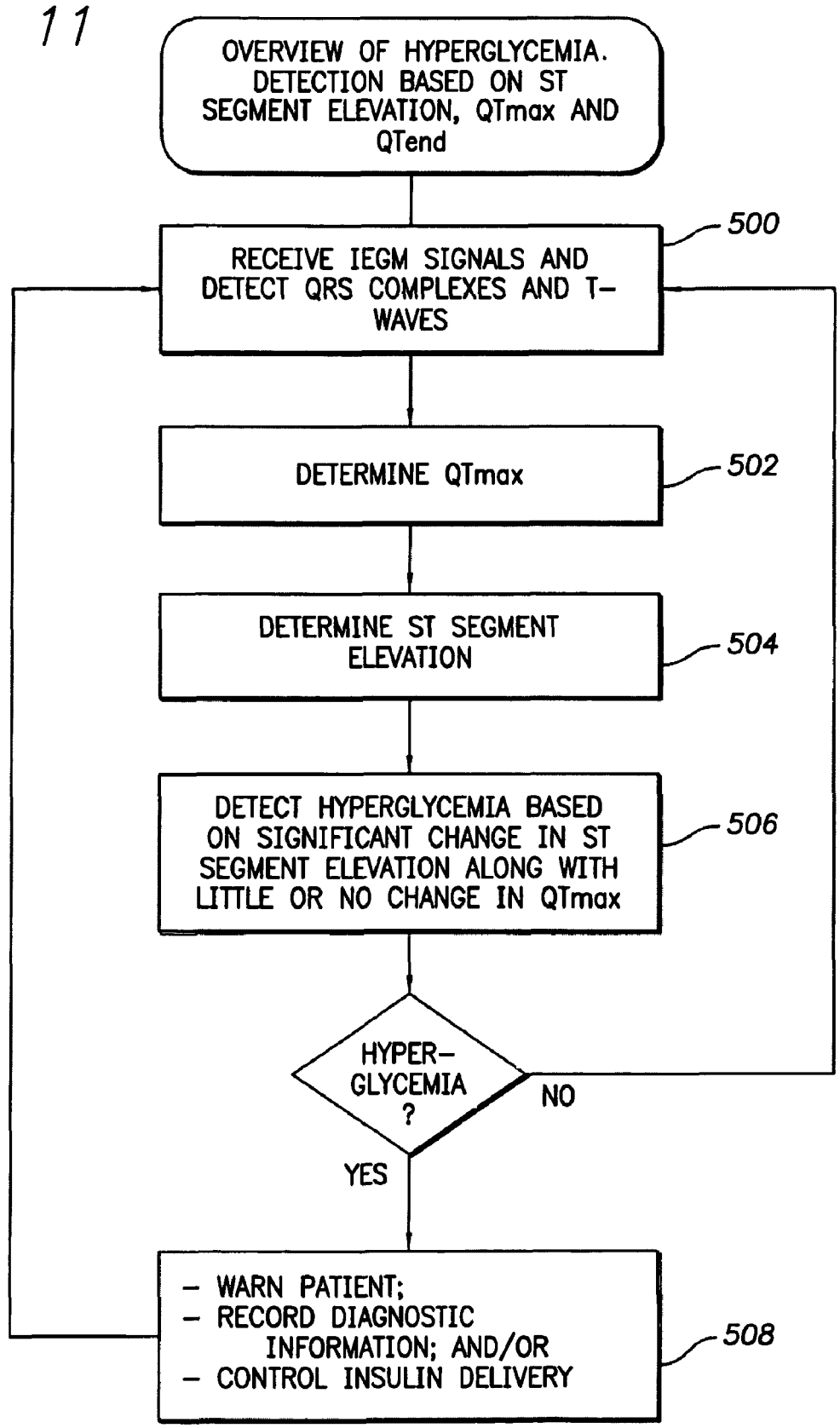
FIG. 11 is a flow chart providing an overview of an exemplary method performed by a hyperglycemia detection system of FIG. 2 for detecting hyperglycemia based primarily on a significant deviation in the ST segment along with little or no change in QTmax.

FIG. 11 provides an overview of hyperglycemia detection techniques performed by the device of FIG. 2. Many aspects of this technique are similar to those of the detection techniques described above and will not be described again in detail. Initially, at step 500, IEGM signals are received and QRS-complexes and T-waves are identified therein. Then, at step 502, QTmax intervals are measured and, at step 504, ST segment elevation is detected. At step 506, the onset of a hyperglycemia is detected based upon detection of a significant change in ST segment elevation along with little or no change in QTmax. A change in ST segment elevation along with a shortening of QTmax is instead indicative of cardiac ischemia. Note that, with hyperglycemia, neither QTmax nor QTend changes significantly. However, a change in ST segment elevation along with little or no change in QTend may also be indicative of either hyperglycemia or cardiac ischemia. So QTmax is observed instead of QTend. As before, data from paced and sensed events should not be combined. QTmax and QTend intervals should be normalized based on heart rate.

Additionally, or in the alternative, values representative of STdeviation, QTmax and QTend may be stored for diagnostic purposes. The device may calculate a single value representative of the risk of hyperglycemia based on a combination of STdeviation, QTmax and QTend, similar to the ischemic burden discussed above. In any case, so long as hyperglycemia is not detected, steps 500-506 are merely repeated. If hyperglycemia is detected, however, the patient is warned, at step 508, and, if properly equipped, the device automatically controls therapy appropriate for responding to hyperglycemia. If an insulin pump is implanted, the pump may be controlled to adjust the dosage of insulin in response to hyperglycemia. Techniques set forth in the patent application of Kroll, listed above, may be suitable for this purpose.

Figure 12:
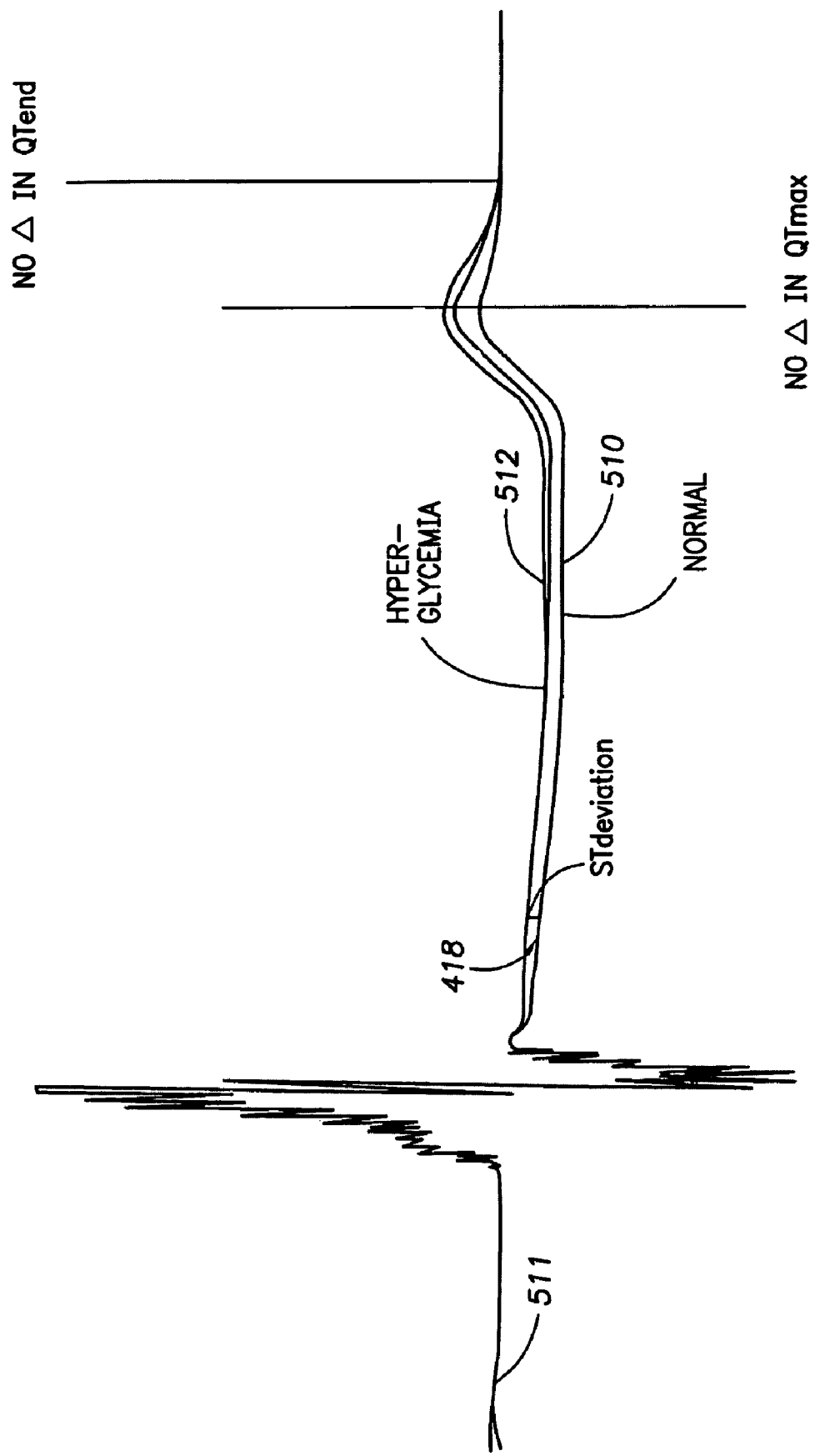
FIG. 12 is a graph providing exemplary representations of the IEGM of a single heart beat, particularly illustrating a significant deviation in ST segment caused by hyperglycemia, along with little or no change in QTmax.

Hence, FIG. 11 provides an overview of a technique that seeks to detect the onset of hyperglycemia based on a combination of STdeviation and QTmax. FIG. 12 illustrates changes in ST segment elevation brought on by hyperglycemia. A first exemplary IEGM trace 510 represents a heartbeat of a healthy patient, i.e. one not subject to hypo/hyperglycemia or cardiac ischemia. A second trace 512 illustrates the heartbeat for a patient with hyperglycemia. As with other traces illustrated herein, the IEGM signals of FIG. 12 are exemplary representations of IEGM signals provided for illustrative purposes only. Comparing the two traces, the elevation of the ST-segment changes. However, there is little or no change in QTmax, i.e. an absolute value of ΔQTmax is near zero. (There is also little or no change in QTend during hyperglycemia, i.e. an absolute value of ΔQTend is also near zero.)

Hence, an examination of QTmax allows the device to properly distinguish a change in ST segment elevation due to hyperglycemia from a change due to hypoglycemia or cardiac ischemia. Compare FIG. 12 with FIGS. 5, 8 and 10, described above. Preferably, any changes in ST segment elevation (as derived from sensed events) and QTmax (as derived from sensed events and normalized based on heart rate) are measured with respect to baseline values of those parameters and values for STdeviation and ΔQTmax are calculated for each heartbeat and averaged over multiple heartbeats. The averaged values are compared against respective thresholds. A warning of hyperglycemia is issued only if STdeviation exceeds its threshold whereas ΔQTmax remains below its thresholds. These thresholds may differ in value from corresponding thresholds discussed above. The various thresholds are programmable values set, for example, based upon respective running averages. Again, multiple thresholds may be defined, in some implementations, to trigger warning signals indicative of different levels of urgency. Routine experimentation may be performed to determine appropriate threshold levels.

What have been described thus far are various techniques for detecting cardiac ischemia, hypoglycemia or hyperglycemia based on various combinations of QTmax, QTend and STdeviation. Preferably, the device is configured to detect any of these conditions and to distinguish therebetween. This is discussed in the following section.

Combined Hypo/Hyperglycemia and Ischemia Detection Examples

Figure 13:
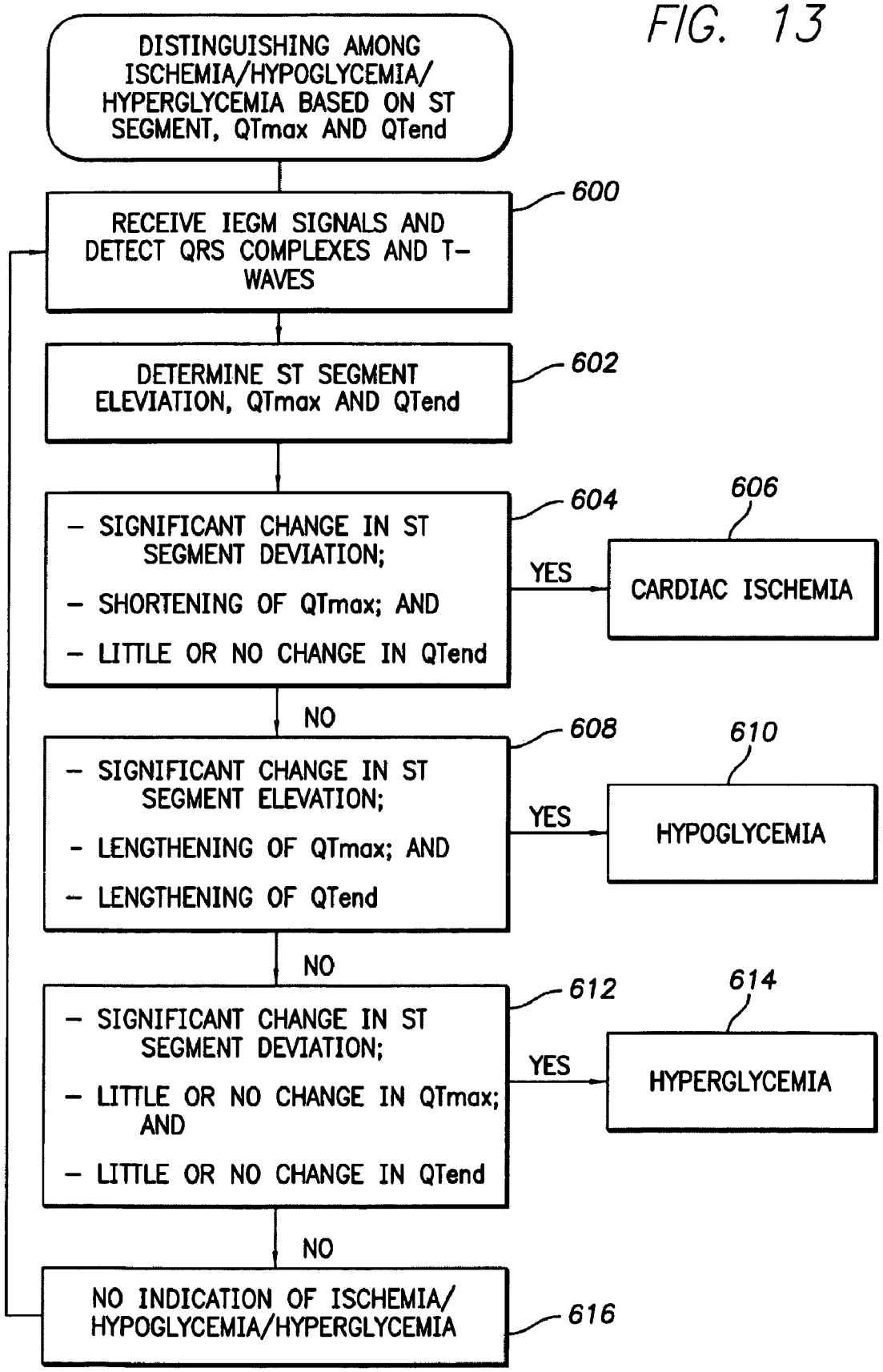
FIG. 13 is a flow chart providing an overview of an exemplary method performed by the implantable device of FIG. 2 for distinguishing among cardiac ischemia, hypoglycemia and hyperglycemia based on ST segment, QTmax, and QTend.

FIG. 13 illustrates an exemplary technique for distinguishing among cardiac ischemia, hypoglycemia and hyperglycemia wherein QTmax, QTend and STdeviation are each examined. Beginning at step 600, the implanted device receives IEGM signals and detect QRS complexes and T-waves. At step 602, the device determines ST segment elevation, QTmax and QTend for each individual heartbeat (as derived from either sensed events only or paced events only and properly normalized based on heart rate). Based upon these values, the device detects and distinguishes between cardiac ischemia, hypoglycemia and hyperglycemia. Briefly, at steps 604-606, the device detects cardiac ischemia based upon any significant change in ST segment elevation (i.e. a significant value for STdeviation) combined with a concurrent shortening of QTmax, so long as there is also little or no change in QTend. At step 608-610, the device detects hypoglycemia based upon any significant change in ST segment elevation combined with a lengthening of both QTmax and QTend. At steps 612-614, the device detects hyperglycemia based upon a significant change in ST segment elevation so long as there is little or no change in either QTmax or QTend. Appropriate warning signals are issued upon detection of ischemia, hypoglycemia or hyperglycemia. The above-described threshold-based techniques may be employed to make these various determinations. Note that the conditions set forth in the steps 604, 608 and 612 are listed above in Table I.

If none of the conditions set forth in steps 604, 608 and 612 are met, then no indication of ischemia, hypoglycemia or hyperglycemia is made, step 616, and processing instead returns to step 604 for examination of additional IEGM signals. In other words, no warning of ischemia, hypoglycemia or hyperglycemia is triggered unless each of the three parameters (STdeviation, QTmax and QTend) corroborates the diagnosis. This differs from the individual examples discussed above wherein an indication of ischemia, hypoglycemia or hyperglycemia may be made based upon significant changes in only one or two of the parameters. By examining all three parameters, a greater degree of reliability and specificity is achieved. Additional detection parameters may be examined as well, including otherwise conventional detection parameters or the parameters set forth in the aforementioned patent applications to Wang et al. and Min et al. IN any case, once the analysis is complete appropriate warnings are issued and therapy is adjusted.

Figure 14:
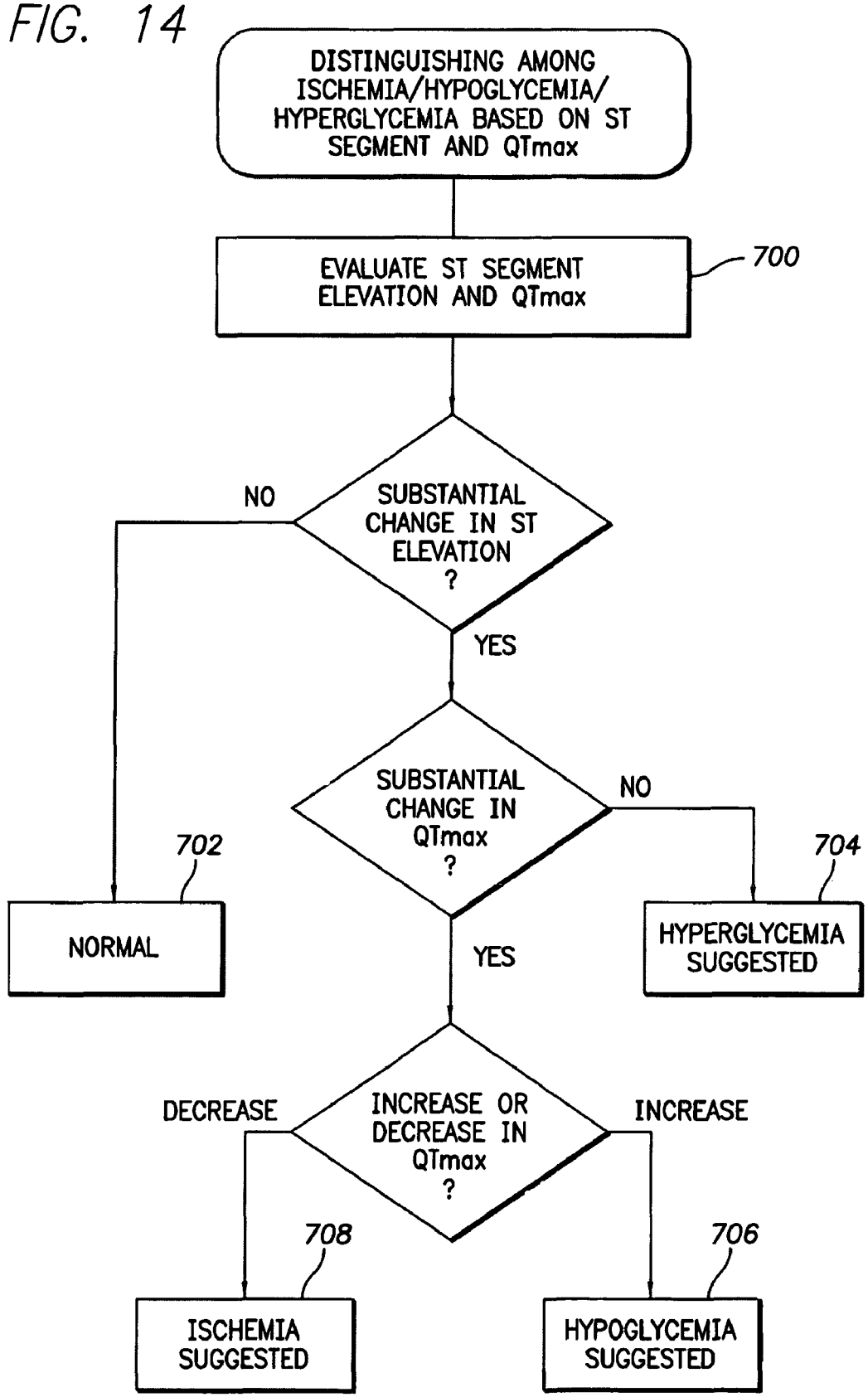
FIG. 14 is a flow chart providing an overview of an exemplary method performed by the implantable device of FIG. 2 for distinguishing among cardiac ischemia, hypoglycemia and hyperglycemia based on ST segment elevation and QTmax.

FIG. 14 illustrates an exemplary technique for distinguishing among cardiac ischemia, hypoglycemia and hyperglycemia based on just QTmax and ST segment elevation. Beginning at step 700, the implanted device evaluates ST segment elevation and ΔQTmax. If there is no substantial change in ST elevation, i.e. STdeviation is small, then the patient's condition is deemed to be normal, at step 702. However, if there has been a substantial change in ST elevation, then the device proceeds to determine whether there has also been a substantial change in QTmax, i.e. whether ΔQTmax exceeds a threshold representative of a significant change. If not, then hyperglycemia is suggested, at step 704. If ΔQTmax exceeds the threshold, however, the device determines whether QTmax has lengthened or shortened. If QTmax has lengthened, then hypoglycemia is suggested that step 706. If QTmax has become shorter, then ischemia is suggested that step 708. The above-described threshold-based techniques may be employed to make these various determinations. Appropriate warning signals are issued and therapy is adjusted.

FIG. 15 illustrates an exemplary technique for distinguishing among cardiac ischemia, hypoglycemia and hyperglycemia based on just QTend and ST segment elevation. Beginning at step 800, the implanted device evaluates ST segment elevation and ΔQTend. As before, if there is no substantial change in ST elevation, i.e. STdeviation is small, then the patient's condition is deemed to be normal, at step 802. If there has been a substantial change in ST elevation, then the device proceeds to determine whether there has also been a substantial change in QTend, i.e. whether ΔQTmax exceeds a threshold representative of a significant change. If not, then ischemia or hyperglycemia are suggested, at step 804, and further analysis may need to be performed to distinguish therebetween (such as by examining QTmax). If ΔQTend exceeds the threshold, however, the device then determines whether QTend has lengthened or shortened. If QTend has lengthened, then hypoglycemia is suggested that step 806. If QTend has instead become shorter, then the analysis is indeterminate, at step 808, perhaps indicative of erroneous data. As already explained, a significant change in ST segment elevation in combination with a significant change in QTend should be associated with lengthening of QTend, not a reduction in QTend. Accordingly, no warnings are issued.) Assuming the analysis is not indeterminate, appropriate warning signals are issued and therapy is adjusted.

What have been described thus far are techniques for distinguishing and detecting hyperglycemia, hypoglycemia and cardiac ischemia based upon various combinations of QTend, QTmax, and ST segment elevation. In the following, an alternative technique particularly for use in distinguishing between hyperglycemia and hypoglycemia will now be described, which is instead based upon an analysis of the amplitudes of P-waves, QRS complexes, and/or T-waves, or other selected electrical events.

Overview of Amplitude-Based Technique for Detecting and Distinguishing Hypoglycemia and Hyperglycemia FIG. 16 provides a high-level overview of the amplitude-based technique of the invention for detecting and distinguishing hyperglycemia and hypoglycemia. Briefly, at step 900, the pacer/ICD of FIGS. 1-2 (or other implantable medical device), detects amplitude-based parameters representative of amplitudes of selected electrical events sensed within the heart of the patient in which the pacer/ICD is implanted. Then, at step 902, the pacer/ICD predicts, detects and distinguishes hypoglycemia and hyperglycemia from one another based on the amplitude-based parameter. In an exemplary embodiment, the selected electrical events include one or more of: P-waves observed within the IEGM, QRS-complexes observed within the IEGM, and/or T-waves observed within the IEGM. The amplitude-based parameter detected at step 900 includes one or more of: the absolute value of the event amplitude; the rate of change of the event amplitude with time; and/or the beat-by-beat change in event amplitude.

The general technique of detecting and distinguishing hypoglycemia and hyperglycemia based upon the amplitude-based parameters of the cardiac electrical events may be used in connection with other hyper/hypoglycemia detection techniques to improve the specificity of those techniques, including the techniques described above, as well as the techniques set forth in the above-reference patents to Kroll and Bharmi. Alternatively, various combinations of the amplitude-based parameters may be used to directly detect hyperglycemia and/or hypoglycemia. This will be a described in greater detail below.

Insofar as hyper/hypoglycemia prediction is concerned, the pacer/ICD includes components for analyzing trends in amplitude-based data to identify periods in time when it is statistically likely that an episode of hyper/hypoglycemia will occur and to issue warning signals in advance thereof. For example, if trend data indicates that the patient frequently has an episode of hyperglycemia early in the morning and data detected during a particular morning indicates that atrial depolarization amplitude is beginning to increase, then a prediction is made by the pacer/ICD that there is a statistical likelihood that an episode of hyperglycemia is imminent and warnings are issued. Trend data may also be used by the physician and patient to aid in the developing a strategy for maintaining glycemic control by, for example, determining the optimal times during the day to eat meals or to take insulin. Also, the rate of change of the amplitude values and the dynamics of separately obtained glucose and insulin profiles may be exploited to identify specific ailments. Otherwise conventional predictive techniques may be applied by the pacer/ICD to the amplitude-based trend data to make the predictions.

FIG. 17 provides a stylized representation of an exemplary IEGM signal 904 illustrating P-wave amplitude 906, QRS-complex amplitude 908, T-wave amplitude 910. The amplitudes may be measured relative to a baseline signal voltage 912 detected, as shown, prior to the P-wave (and subsequent to the T-wave of the preceding cardiac cycle, not separately shown.) Since the polarity of the IEGM signal may be arbitrary, the absolute values of the amplitudes are preferably used. Although the amplitudes of P-waves, QRS-complexes and T-waves are preferably exploited, the amplitudes of the other electrical events observed within cardiac electrical signals could potentially be exploited as well, assuming that there is a correlation between changes in the amplitudes of those events and the glycemic state of the patient.

Turning now to FIG. 18, an example of the general technique of the FIG. 16 will now be described, which exploits P-waves, QRS-complexes and T-waves. Beginning at step 1000, the pacer/ICD of FIGS. 1-2 (or other implantable medical device) inputs IEGM signals from the heart of the patient in which the device is implanted and detects P-waves, QRS-complexes and T-waves within the IEGM signals. Detection of these electrical events may be performed using otherwise conventional detection techniques. Insofar as the T-wave is concerned, T-wave detection techniques set forth in the above referenced patent applications of Min et al. and Wang et al., may be exploited to improve T-wave detection specificity. At step 1002, the pacer/ICD determines the absolute values of the amplitudes and the rates of change, if any, in the amplitudes, either is a function of time or beat by beat.

At step 1004, the pacer/ICD then detects the onset of hyperglycemia, if occurring within the patient, based on any significant and rapid increase in P-wave amplitude and any significant and rapid increase in QRS complex amplitude, in combination with a lack of significant increase in T-wave amplitude. At step 1006, the pacer/ICD detects the onset of hypoglycemia, if occurring within the patient, based on any significant and rapid increase in T-wave amplitude along with a moderately rapid increase in QRS complex amplitude to moderately elevated levels, in combination with a lack of significant increase in P-wave amplitude.

FIGS. 19-22 illustrate changes in the various amplitude-based parameters occurring during experimentally induced episodes of hyperglycemia and hypoglycemia within canine test subjects. More specifically, FIG. 19 illustrates the changes in blood glucose levels occurring during episodes of hyperglycemia and hypoglycemia. A first trace 1008 illustrates changes in blood glucose level during an episode of hyperglycemia induced by infusion of excess blood glucose into a non-diabetic human test subject. The vertical axis of the graph illustrates blood glucose levels in milligrams/deciliter (mg/dL). A horizontal axis of graph is a time axis that specifically identifies various points at which blood glucose levels were measured. Point 1 represents a baseline blood glucose level, point 2 represents a time seven minutes from infusion, and point 3 represents a time 17 minutes from infusion. As can be seen, there is a significant increase in blood glucose levels during the first seven minutes, followed by a partial reduction as the test subject's body begins to process the excess blood glucose levels, i.e. the body's compensatory mechanisms begin to take effect. A second trace 1010 of FIG. 19 illustrates changes in blood glucose level during an episode of hypoglycemia induced by injecting excess insulin into the same canine test subject. As can be seen, there is a measurable decrease in blood glucose levels during the first seven minutes, followed by continued reduction in blood glucose levels over the next ten minutes, at the additional insulin in the test subject's body continues to cause a depletion in blood glucose levels.

FIG. 20 illustrates changes in P-wave amplitude measured during the episodes of hyperglycemia and hypoglycemia illustrated in FIG. 19. The vertical axis illustrates the absolute value of the P-wave amplitude in millivolts (mV). The horizontal time axis illustrates the same points as in FIG. 19. Trace 1012 illustrates changes in P-wave amplitude during hyperglycemia; whereas trace 1014 illustrates the general lack of change in amplitude during hypoglycemia. As can be seen, there is a significant increase in P-wave amplitude associated with hyperglycemia, which is manifested both in terms of a significant increase in the absolute value of the P-wave amplitude, as well as a rapid rate of change of P-wave amplitude. P-wave amplitude increases, in the example, by nearly 0.8 mV over a period of only seventeen minutes. In contrast, there is little or no change in P-wave amplitude during hypoglycemia. Hence, FIG. 20 illustrates that a significant and rapid increase in P-wave amplitude is associated with hyperglycemia; whereas a lack of change in P-wave amplitude is associated with hypoglycemia.

FIG. 21 illustrates changes in QRS-complex amplitude measured during the episodes of hyperglycemia and hypoglycemia illustrated in FIG. 19. The vertical axis illustrates the absolute value of the QRS-complex amplitude in mV. The horizontal time axis illustrates the same points as in FIG. 19. Trace 1016 illustrates changes in QRS-complex amplitude during hyperglycemia; whereas trace 1018 illustrates change during hypoglycemia. As can be seen, there is a significant increase in QRS-complex amplitude associated with hyperglycemia, which is manifested both in terms of a significant increase in the absolute value of the QRS-complex amplitude, as well as a rapid rate of change of QRS-complex amplitude. QRS-complex amplitude increases, in the example, by nearly 1.0 mV over a period of only 17 minutes. In contrast, there is a less significant increase in QRS-complex amplitude during hypoglycemia, of less than about 0.6 mV. Hence, FIG. 21 illustrates that a significant and rapid increase in QRS-complex amplitude is associated with hyperglycemia; whereas a more moderate and less rapid increase in QRS-complex amplitude is associated with hypoglycemia.

FIG. 22 illustrates changes in T-wave amplitude measured during the episodes of hyperglycemia and hypoglycemia illustrated in FIG. 19. The vertical axis illustrates the absolute value of the T-wave amplitude in mV. The horizontal time axis again illustrates the same points as in FIG. 19. Trace 1020 illustrates changes in T-wave amplitude during hyperglycemia; whereas trace 1022 illustrates changes during hypoglycemia. As can be seen, there is a significant increase in T-wave amplitude associated with hypoglycemia, which is manifested both in terms of a significant increase in the absolute value of the T-wave amplitude, as well as a rapid rate of change of T-wave amplitude. T-wave amplitude increases, in the example, by nearly 1.0 mV over a period of only seventeen minutes. In contrast, there is little or no change in T-wave amplitude during hyperglycemia. More specifically, there is a slight increase in T-wave amplitude observed at the seven minute mark during hyperglycemia, followed by a reduction back to baseline levels over the next ten minutes. Hence, FIG. 22 illustrates that a significant and rapid increase in T-wave amplitude is associated with hypoglycemia; whereas a general lack of change in T-wave amplitude is associated with hyperglycemia.

Thus, FIGS. 19-22 illustrate changes in amplitudes of P-waves, QRS-complexes and T-waves within canine test subjects arising as a result of changes in the glycemic state of test subject. It is believed that similar changes occur in humans. For the purposes of the invention, a significant increase in an amplitude value may be detected by comparing current amplitude values against running averages of previous amplitude values to determine differences therebetween, which are then compared against predetermined threshold values indicative of the onset of hyperglycemia or hypoglycemia. In this regard, separate amplitude threshold values are predetermined for P-wave amplitude, QRS-complex amplitude, and T-wave amplitude. Insofar as hyperglycemia is concerned, the amplitude threshold values for P-wave amplitude and QRS complex amplitude represent upper thresholds, above which hyperglycemia is indicated. The amplitude threshold value for T-wave amplitude represents a lower threshold, below which hyperglycemia is confirmed. Insofar as hypoglycemia is concerned, the rate threshold values for T-wave amplitude represents an upper threshold, above which hypoglycemia is indicated. The amplitude threshold value for P-wave amplitude represents a lower threshold, below which hypoglycemia is confirmed. For hypoglycemia, the amplitude threshold value for the QRS-complex amplitude represents an intermediate threshold. If the QRS-complex amplitude exceeds the intermediate hypoglycemia threshold but not the upper hyperglycemia threshold, then hypoglycemia is indicated. If the QRS-complex amplitude exceeds both intermediate hypoglycemia threshold and the upper hyperglycemia threshold, then hyperglycemia is instead indicated.

A rapid increase in the amplitude value of an electrical event (such as the P-wave) may be detected by calculating the rate of change of amplitude values (either as a function of time or as a beat by beat change), then comparing the rate of change against predetermined threshold values indicative of the onset of hyperglycemia or hypoglycemia. Again, separate rate threshold values are predetermined for P-wave amplitude changes, QRS-complex amplitude changes and T-wave amplitude changes. Given that hyperglycemia is associated with a lack of significant increase in T-wave amplitude, it is unnecessary to calculate a rate of change in T-wave amplitude for the purposes of confirming hyperglycemia. Likewise, given that hypoglycemia is associated with a lack of significant increase in P-wave amplitude, it is unnecessary to calculate a rate of change in P-wave amplitude for the purposes of confirming hypoglycemia.

Preferably, the various amplitude-based threshold values are expressed as percentages of the running average values. In one example, an increase of over a predetermined upper threshold percentage of the running average of a given amplitude parameter (such as P-wave amplitude or T-wave amplitude) is deemed to represent a significant increase. An increase of over predetermined intermediate threshold percentage of the running average of a given amplitude parameter (such as the QRS-complex amplitude) is deemed to represent a moderate increase. An increase of less than predetermined lower threshold percentage over the running average is deemed to be indicative of lack of increase. Likewise, preferably, the rate-based threshold values are expressed as percent values.

Appropriate values for the various thresholds used for detecting and distinguishing hyperglycemia and hypoglycemia may be determined in advance through otherwise routine experimentation. For example, studies may be performed for various classes of patients (based on, for example, gender, age, medical condition, weight, etc.) to determine threshold values that may be appropriate for use with those classes of patients. Following implant of the pacer/ICD, a physician or other medical professional inputs the age, gender, weight, etc. for the patient into the external programmer, which then looks up the appropriate threshold values from tables stored therein and transmits those values to the pacer/ICD for use therein. Alternatively, the threshold values may be individually set for particular patients. In one example, the physician briefly induces episodes of hyperglycemia and hypoglycemia within the patient and records and monitors changes in the various amplitude values, from which suitable threshold values for use with that particular patient are then derived. The threshold values are then programmed into the pacer/ICD of the particular patient via the external programmer device.

In any case, if hyperglycemia is indicated then, step 1024 of FIG. 18 is performed wherein the pacer/ICD responds to the newly detected episode of hyperglycemia. The specific response depends upon the capabilities of the implanted system and the needs of the particular patient. If insulin is being automatically delivered to an insulin-dependent diabetic via an implantable drug pump then delivery of insulin is increased in response to hyperglycemia. Preferably, any hyperglycemia-related conditions of the patient (such as diabetes) are diagnosed in advance by the physician and the resulting diagnosis is programmed into the implanted pacer/ICD by the physician for use in controlling therapy. At step 1024, appropriate warning signals are generated via an implanted warning device or external bedside monitor. Such warning signals are particularly desirable within implantable systems not equipped to provide any automatic hyperglycemia therapy. For example, if patient is an insulin-dependent diabetic, but no implantable insulin pump is provided, then warning signals are provided to alert the patient to manually take insulin.

Preferably, the warning signals are of sufficient magnitude to awaken the patient, if sleeping. The magnitude of the warning signals may be controlled based upon the time of day or the activity state of the patient so as to be of greater magnitude if the patient appears to be resting or sleeping. Otherwise conventional sleep detectors may also be employed in this regard. In one example, once a subcutaneous warning signal is perceived, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal. Upon confirmation of the warning, the patient then takes appropriate actions, such as taking insulin. Warning devices of this type are discussed in U.S. patent application Ser. No. 10/603,429, of Wang et al., entitled "System and Method for Detecting Cardiac Ischemia Using an Implantable Medical Device." Also, preferably, any warning signals transmitted to a bedside monitor are then conveyed to medical personal via any suitable communication network, particularly if the patient is in a hospital, rest home or the like where medical personnel can easily summoned.

If hypoglycemia is instead indicated then, step 1026 of FIG. 18 is performed wherein the pacer/ICD responds to the episode of hypoglycemia. Again, the specific response depends upon the capabilities of the implanted system and the needs of the particular patient. If insulin is being automatically delivered to an insulin-dependent diabetic via an implantable drug pump then delivery of insulin is suspended so as to prevent additional insulin from exacerbating the hypoglycemia. On the other hand, if the patient has been diagnosed with hyperinsulinism, delivery of appropriate medications such as sulfonylureas, meglitinides, biguanides, thiazolidinediones, or alpha glucosidase inhibitors, may be initiated using an implantable drug pump (assuming such drugs are suitable for automatic delivery via a drug pump.) At step 1026, the pacer/ICD also preferably begins charging its defibrillation capacitors in expectation of delivery of shocks in the event that the episode of hypoglycemia triggers ventricular fibrillation. Appropriate warning signals are generated via an implanted warning device or external bedside monitor. Such warning signals are particularly desirable within implantable systems not equipped to provide any automatic hypoglycemia therapy. For example, if patient is an insulin-dependent diabetic, then warning signals are provided to alert the patient to take a suitable number of sugar pills or other substances or medications sufficient increase blood glucose levels.

Note that, typically, the detection of hyper/hypoglycemia is disabled during an arrhythmia as some arrhythmias may affect the relative amplitudes of the various cardiac electrical events so as to prevent reliable detection of hyper/hypoglycemia.

Also, note that, in many cases, a detectable change in the amplitude-based parameters analyzed in accordance with the invention occurs even before an episode of hyper/hypoglycemia actually begins, thus allowing for prediction of the episode and allowing for an early warning to be issued to the patient.

Thus, FIG. 18 illustrates an exemplary method for detecting and distinguishing hyperglycemia and hypoglycemia. Depending upon the particular implementation, the pacer/ICD may be configured just to distinguish between hyperglycemia and hypoglycemia as an adjunct to other hyper/hypoglycemia techniques, such as those described above with references to of FIGS. 1-18. For example, the pacer/ICD may be programmed merely to analyze P-wave amplitudes as a means for distinguishing hyperglycemia from hypoglycemia so as to improve the specificity of another glycemic state detection technique. In other examples, pacer/ICD may be programmed merely to analyze P-wave amplitudes or QRS-complex amplitudes to improve the specificity of other detection techniques. In general, any of the individual parameters discussed with reference to FIG. 18 may be employed to aid in distinguishing hyperglycemia from hypoglycemia. Hence, it is not necessary for the pacer/ICD to detect or analyze all of the above-described parameters. In some cases, only a single parameter is analyzed to aid in distinguishing hyperglycemia and hypoglycemia. In other cases, two or more parameters are analyzed. As already denoted, an analysis of P-wave amplitudes in combination with T-wave amplitude is particularly effective for use in distinguishing hyperglycemia from hypoglycemia, since P-waves and T-waves respond oppositely to hyperglycemia and hypoglycemia.

In other implementations, however, the pacer/ICD is programmed to directly detect hyperglycemia and/or hypoglycemia based upon various combinations of the aforementioned parameters. In other words, the techniques described herein are not merely used as an aid in distinguishing hyperglycemia from hypoglycemia, but are instead used to directly detect such conditions. In particular, a significant increase in P-wave amplitude and/or a significant increase into QRS-complex amplitude, in combination with a lack of significant change in T-wave amplitude is sufficient to detect the onset of hyperglycemia. Improved specificity may be achieved by examining both P-wave amplitude and QRS-complex amplitude, though only one or the other is typically sufficient within most patients. Insofar as hypoglycemia is concerned, a significant increase in T-wave amplitude in combination with a lack of change in P-wave amplitude is sufficient to detect the onset of hypoglycemia. Improved specificity may be achieved by additionally examining QRS-complex amplitudes to verify that the QRS-complex amplitude exhibits a moderate increase.

In general, a wide variety of techniques can be implemented consistent with the principles the invention and no attempt is made herein to describe all possible techniques. Although described primarily with reference to an example wherein the implanted device is a defibrillation/pacer, principles of the invention are applicable to other implantable medical devices as well. In addition, whereas the techniques described herein are performed by the implanted device, the techniques may alternatively be performed by an external device using IEGM signals or other signals transmitted from the implanted device. For example, a bedside monitor may be configured to receive IEGM signals from the implanted device via "long-range" telemetry then analyze the signals using the aforementioned techniques and issue any appropriate warnings. Alternatively, the bedside monitor may transmit the IEGM data to a central server or other central processing device, which analyzes data from multiple patients to detect ischemia, hypoglycemia or hyperglycemia within any of those patients. In such an implementation, the central processing device then transmits appropriate warning signals to the bedside monitor of the patient for warning the patient and then additionally transmits appropriate warning signals to the physician associated with the patient or a third party such as emergency medical service (EMS) personnel. A system incorporating bedside monitoring units connected to a centralized external programmer system is described in U.S. Patent Application Serial Number 2002/0143372, of Snell et al., entitled "System and Method for Remote Programming of Implantable Cardiac Stimulation Devices", published Oct. 3, 2002.

The various functional components of the exemplary systems described herein may be implemented using any appropriate technology including, for example, microprocessors running software programs or application specific integrated circuits (ASICs) executing hard-wired logic operations. In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for use with an implantable medical device for detecting one of hypoglycemia and hyperglycemia within a patient in which the device is implanted, said method comprising:
    tracking with the implantable medical device, rates of change of ventricular repolarization amplitudes and at least one of atrial depolarization amplitudes and ventricular depolarization amplitudes and ventricular repolarization amplitudes;
    detecting with the implantable medical device, an onset of hyperglycemia upon detecting a rapid increase in at least one of the rate of change of atrial depolarization amplitudes and ventricular depolarization amplitudes; and
    detecting with the implantable medical device, an onset of hypoglycemia upon detecting a rapid increase in the rate of change of ventricular repolarization amplitudes.

2. The method of claim 1 wherein detecting a rapid increase in at least one of the rate of change of atrial depolarization amplitudes and ventricular depolarization amplitudes comprises:
    calculating a rate of change for at least one of atrial depolarization amplitudes and ventricular depolarization amplitudes;
    comparing the calculated rate of change with a predetermined threshold rate of change indicative of the onset of hyperglycemia; and
    detecting hyperglycemia when the calculated rate of change exceeds the predetermined threshold rate of change.

3. The method of claim 2 wherein the calculated rate of change is calculated over a period of time.

4. The method of claim 2 wherein the calculated rate of change is calculated on a beat by beat basis.

5. The method of claim 1 wherein detecting a rapid increase in the rate of change of ventricular repolarization amplitudes comprises:

calculating a rate of change for ventricular repolarization amplitudes;
comparing the calculated rate of change with a predetermined threshold rate of change indicative of the onset of hypoglycemia; and
detecting hypoglycemia when the calculated rate of change exceeds the predetermined threshold rate of change.

6. The method of claim 5 wherein the calculated rate of change is calculated over a period of time.

7. The method of claim 5 wherein the calculated rate of change is calculated on a beat by beat basis.

8. The method of claim 1 further comprising, upon detecting an onset of hyperglycemia, confirming hyperglycemia by:
calculating a rate of change for ventricular repolarizations; and
determining that the rate of change corresponds to a lack of significant change in ventricular repolarization amplitudes.

9. The method of claim 1 further comprising, upon detecting an onset of hypoglycemia, confirming hypoglycemia by:
calculating a rate of change for atrial depolarizations; and
determining that the rate of change corresponds to a lack of significant change in atrial depolarization amplitudes.

10. An implantable medical device comprising:
a detector operative to detect ventricular repolarization amplitudes and at least one of atrial depolarization amplitudes and ventricular depolarization amplitudes; and
a processor operative to:
track rates of change of ventricular repolarization amplitudes and at least one of atrial depolarization amplitudes and ventricular depolarization amplitudes;
detect an onset of hyperglycemia upon detecting a rapid increase in at least one of the rate of change of atrial depolarization amplitudes and ventricular depolarization amplitudes; and
detect an onset of hypoglycemia upon detecting a rapid increase in the rate of change of ventricular repolarization amplitudes.

* * * * *